United States Patent
Azar

(10) Patent No.: US 6,214,034 B1
(45) Date of Patent: *Apr. 10, 2001

(54) METHOD OF SELECTIVE PHOTOTHERMOLYSIS

(75) Inventor: Zion Azar, Shoham (IL)

(73) Assignee: Radiancy, Inc., Orangeburg, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/076,098

(22) Filed: May 12, 1998

Related U.S. Application Data

(63) Continuation-in-part of application No. 08/707,562, filed on Sep. 4, 1996, now Pat. No. 5,759,200.

(51) Int. Cl.[7] .................................................. A61N 33/00
(52) U.S. Cl. .................................. 607/89; 607/90; 606/9; 606/27; 606/32
(58) Field of Search ................................ 607/89, 88, 90, 607/96, 100; 606/1, 2, 9, 10, 11, 12, 13, 27, 30, 31, 32, 33, 34, 41, 42

(56) References Cited

U.S. PATENT DOCUMENTS

| | | | |
|---|---|---|---|
| 3,901,247 | * 8/1975 | Walmsley | 607/29 |
| 3,934,115 | 1/1976 | Peterson . | |
| 4,026,284 | * 5/1977 | Boehringer | 128/205.24 |
| 4,604,992 | 8/1986 | Sato . | |
| 4,686,986 | 8/1987 | Fenyo et al. . | |
| 4,829,262 | 5/1989 | Furumoto . | |

(List continued on next page.)

FOREIGN PATENT DOCUMENTS

| | | |
|---|---|---|
| 400 305 | 12/1995 | (AT) . |
| 0 172 490 | 2/1986 | (EP) . |
| 0 736 308 | 10/1996 | (EP) . |
| WO 91/15264 | 10/1991 | (WO) . |

OTHER PUBLICATIONS

McDaniel, D.H., "Cutaneous Vascular Disorders: Advances in Laser Treatment", CUTIS, vol. 45, pp. 339–360. May, 1990.

Hurwitz, R.M. et al, "Port Wine Stain: A New Therapeutic Approach to an Old Birth Defect", Indiana Medicine, pp. 336–339, May , 1990.

(List continued on next page.)

Primary Examiner—Linda C. M. Dvorak
Assistant Examiner—R. Kearney
(74) Attorney, Agent, or Firm—Fenster & Company Patent Attorneys Ltd.

(57) ABSTRACT

A method and apparatus for selective photothermolysis of a target tissue within surrounding tissue. The target and the surrounding tissue are heated to a predetermined temperature of about 60° C. by a pulsed heat source such as a flash lamp which creates a temperature gradient in the air included in a cavity formed between the housing of the apparatus and the surrounding tissue. The surface temperature of the tissue is monitored by a sensor unit. When the tissue surface reaches the predetermined temperature the target tissue is heated to the point of coagulation, preferably by narrow band electromagnetic radiation. The temperature difference between the coagulating target and the surrounding tissue is sufficiently mild that heat diffusing out of the target does not damage the surrounding tissue, even in the case of a relatively large target such as varicose veins. The heating action may be terminated by automatically pumping air or another suitable coolant into the cavity when the surface of the tissue reaches a preset value or by lifting the apparatus off the tissue. The apparatus may include a programmable controller which may be programmed locally or remotely with the treatment parameters.

89 Claims, 13 Drawing Sheets

U.S. PATENT DOCUMENTS

| | | |
|---|---|---|
| 5,057,104 | 10/1991 | Chess. |
| 5,066,293 | 11/1991 | Furumoto. |
| 5,071,417 | 12/1991 | Sinofsky. |
| 5,312,395 | 5/1994 | Tan et al.. |
| 5,344,418 | 9/1994 | Ghaffari. |
| 5,441,531 | 8/1995 | Zarate et al.. |
| 5,521,392 | 5/1996 | Kennedy et al.. |
| 5,595,568 | 1/1997 | Anderson et al.. |
| 5,604,629 | 2/1997 | Hunter et al.. |
| 5,653,706 | 8/1997 | Zavislan et al.. |
| 5,720,772 | 2/1998 | Eckhouse. |
| 5,759,200 | 6/1998 | Azar. |
| 5,814,008 * | 9/1998 | Chen et al. ............................ 604/21 |
| 5,824,023 * | 10/1998 | Anderson ............................... 607/88 |
| 5,853,408 * | 12/1998 | Muni ..................................... 606/27 |
| 5,868,731 * | 2/1999 | Budnik et al. ......................... 606/9 |
| 5,989,246 * | 11/1999 | Kaufmann et al. .................... 606/15 |

OTHER PUBLICATIONS

Tan, O.T. et al, "585nm for the Treatment of Port–Wine Stains", Plastic and Reconstructive Surgery, pp. 1112–1117, Dec. 1990.

Kurban, A.K. et al, "The Importance of Pulse Duration in Laser—Tissue Interactions: A Histological Study".

Anderson, R.R. et al, "Selective Photothermolysis: Precise Microsurgery by Selective Absorption of Pulsed Radiation", Science, vol. 220, pp. 524–527, Apr. 29, 1983.

Internet Web Site for the Institute for Dermatology and Cosmetic Surgery 6 pages.

Candela Corp news release—"Candela Expands Skin Laser Product Line", 4 pages.

Candela Corp website advertisement—2 pages.

U.S. Federal Trade Commision—Website—Varicose Veins Treatment, 4 pages.

* cited by examiner

METHOD OF SELECTIVE PHOTOTHERMOLYSIS

RELATIONSHIP TO OTHER U.S. APPLICATIONS

This Application is a continuation-in-part of U.S. patent application Ser. No. 08/707,562, filed Sep. 4, 1996, now U.S. Pat. No. 5,759,200.

FIELD OF THE INVENTION

The present invention relates to dermatological surgery and, more specifically, to a method of selective photothermolysis that allows the destruction of targets, such as varicose veins, that are too large to be destroyed by presently known methods without damaging the surrounding healthy tissue, and targets such as plaque psoriasis.

BACKGROUND OF THE INVENTION

Selective photothermolysis is a surgical method, introduced by Anderson and Parrish in 1983 ("Selective Photothermolysis: Precise Microsurgery by Selective Absorption of Pulsed Radiation", Science, Vol. 220, pp. 524–527), for destroying certain diseased or unsightly tissue, on or near the skin, with minimal damage to the surrounding healthy tissue. The tissue to be destroyed must be characterized by significantly greater optical absorption at some wavelength of electromagnetic radiation than the surrounding tissue. The method consists of irradiating the target and the surrounding tissue with pulsed electromagnetic radiation, usually visible radiation, that is preferentially absorbed by the target. The energy and duration of the pulses is such that the target is heated to between about 70° C. and about 80° C., at which temperature the proteins of the target coagulate. Because the target absorbs the incident radiation much more strongly than the surrounding tissue, the surrounding tissue is heated negligibly.

Usually, the radiation source is a laser, for example a flashlamp-pulsed dye laser. A laser source has the advantage of being inherently monochromatic. Other sources include broad band sources used in conjunction with narrow band filters, as described, for example, by Gustaffson in Patent No. WO 91/15264. A similar device, called the "Photoderm-VL", is manufactured by ESC Medical Systems.

Suitable targets for selective photothermolysis include birthmarks, port-wine stains, spider veins, and varicose veins, all of which tend to be much redder than the surrounding tissue because of their higher concentration of oxyhemoglobin-containing red blood cells. Anderson and Parrish used light of a wavelength of 577 nanometers, corresponding to the 577 nanometer oxyhemoglobin absorption band. It was subsequently determined (Tian, Morrison, and Kurban, "585 nm for the Treatment of Port-Wine Stains", Plastic and Reconstructive Surgery, vol. 86 no. 6 pp. 1112–1117) that 585 nanometers is a more effective wavelength to use.

One constraint on the pulse duration is that the surrounding tissue must not be heated to the point that it, too, begins to coagulate. As the target is heated, heat begins to diffuse from the target to the cooler surrounding tissue. To keep the surrounding tissue from being heated to the point of damage, the pulse length must be kept on the order of the target's thermal relaxation time. For relatively small targets, such as birthmarks, port-wine stains, and spider veins, typical pulse lengths are on the order of hundreds of microseconds. For varicose veins, pulse lengths on the order of milliseconds should be used.

A complication arises in the treatment of varicose veins by selectiv photothermolysis. The normal tissue surrounding varicose veins typically includes other blood vessels, notably capillaries, that also absorb the incident radiation but, being much smaller than the varicose veins, have much shorter thermal relaxation times. Therefore, heat diffusing from these other blood vessels into the surrounding tissue tends to heat the surrounding tissue to the point of damage, thereby causing scarring. Recently, selective photothermolysis also has been used to treat psoriatic skin tissue.

Psoriasis is a non contagious skin disorder that most commonly appears as inflamed swollen skin lesions covered with silvery white scale. This most common type of psoriasis is called "plaque psoriasis".

Psoriasis comes in many different variations and degrees of severity. Different types of psoriasis display characteristics such as pus-like blisters (pustular psoriasis), severe sloughing of the skin (erythrodermic psoriasis), drop-like dots (guttate psoriasis) and smooth inflamed legions (inverse psoriasis). The degrees of severity of psoriasis are divided into three important categories: mild, moderate and severe.

Skin cells are programmed to follow two possible programs: normal growth or wound healing. In a normal growth pattern, skin cells are created in the basal cell layer, and then move up through the epidermis to the stratum corneum, the outermost layer of the skin. Dead cells are shed from the skin at about the same rate as new cells are produced, maintaining a balance. This normal process takes about 28 days from cell birth to death.

When skin is wounded, a wound healing program is triggered, also known as regenerative maturation. Cells are produced at a much faster rate, theoretically to replace and repair the wound. There is also an increased blood supply and localized inflammation. In many ways, psoriatic skin is similar to skin healing from a wound or reacting to a stimulus such as infection.

Lesional psoriasis is characterized by cell growth in the alternate growth program. Although there is no wound at a psoriatic lesion, skin cells, also referred to as keratinocytes, behave as if there is. These keratinocytes switch from the normal growth program to regenerative maturation. Cells are created and pushed to the surface in as little as 2–4 days, and the skin cannot shed the cells fast enough. The excessive skin cells build up and form elevated, scaly lesions. The white scale (called "plaque") that usually covers the lesion is composed of dead skin cells, and the redness of the lesion is caused by increased blood supply to the area of rapidly dividing skin cells.

There is thus a widely recognized need for a method and a device adapted for home use by a patient for selective photothermolysis that is effective in removing larger surgical targets, such as varicose veins, without peripheral damage, and that can be used in treatment of psoriasis.

SUMMARY OF THE INVENTION

According to the present invention there is provided a method of selective photothermolysis of a target within surrounding tissue, comprising the steps of: (a) heating the target and the surrounding tissue above normal body temperature; and (b) heating the target to between about 70° C. and about 80° C.

According to the present invention there is provided a device for selective photothermolysis of a target within surrounding tissue, comprising: (a) means for generating broad-band electromagnetic radiation; and (b) means for generating at least one pulse of substantially monochromatic electromagnetic radiation, each of said at least one pulse being substantially simultaneous with said broad-band electromagnetic radiation.

The method of the present invention is based on the fact that the rate of heat diffusion from a warm body to a cold body is proportional to the thermal gradient between the bodies. Therefore, heating the surrounding tissue to a temperature higher than normal body temperature, but not high enough to cause damage, and only then heating the target to the point of coagulation, creates an environment in which the thermal gradient between the target and the surrounding blood vessels, on the one hand, and the other surrounding tissue, on the other hand, is sufficiently small that the surrounding tissue is not damaged. In the context of the present invention, "higher than normal body temperature" means a temperature of at least about 40° C., but preferably between about 55° C. and about 65° C. Furthermore, the pulse of monochromatic light used to heat the target may be of lower power and shorter duration than in the prior art, because the target is heated from a higher initial temperature.

The device of the present invention accomplishes this end by heating the surrounding tissue using broad-band electromagnetic radiation. The scope of the present invention includes all effective wavelengths of electromagnetic radiation, and effective spectral bands for this purpose include microwave radiation; but the preferred spectral band, both for heating the surrounding tissue and for heating the target itself, is visible radiation. The preferred device for generating the broad-band (white) light is a high intensity lamp such as a xenon arc lamp. The device includes a mechanism for pulsing the light from the lamp. This mechanism may include circuitry for controlling the current supplied to the lamp (e.g., the mechanism may operate by turning the lamp on and off); or may include a mechanical shutter.

There are two preferred means for generating the substantially monochromatic radiation used to heat the target. The first is a laser that operates at the desired wavelength, preferably a wavelength between about 570 nanometers and about 610 nanometers. The second is to pass light from the high intensity lamp through a suitable wavelength selection device, such as a narrow band filter or a monochromator.

The device of the present invention synchronizes the monochromatic pulses with the broad-band electromagnetic radiation, by means well-known in the art, to ensure that the surrounding tissue has been heated sufficiently before the monochromatic pulse is turned on to heat the target further, and to ensure that the target is heated further before the surrounding tissue has a chance to cool down. In general terms, this means that, if the broad-band electromagnetic radiation is pulsed, then each monochromatic pulse is substantially simultaneous with a broad-band pulse. As used herein "substantially simultaneous" means that the monochromatic pulse is turned on either while the broad-band pulse is on, or substantially immediately after the broad-band pulse is turned off.

There is also provided, in accordance with a preferred embodiment of the present invention, apparatus for selective photothermolysis of a target tissue within the skin. The apparatus includes a housing having an opening therein. The housing formes a cavity enclosing a volume of air when the opening is placed in contact with the skin. The apparatus further includes a pulsable heat source disposed within the housing for rapidly heating the volume of air to form a temperature gradient therealong. The apparatus further includes a pulsable source of narrow band electromagnetic radiation disposed within the housing for irradiating the skin with narrow band electromagnetic radiation to selectively heat the target tissue. The apparatus further includes a sensing unit attached to the housing for sensing the temperature of the skin. The apparatus further includes a controller unit connected to the heat source, the source of electromagnetic radiation and the sensor unit for controlling the heat source and the source of electromagnetic radiation. The controller coordinates the sequence of activation of the heat source and the source of electromagnetic radiation and receives signals from the sensor unit. The apparatus further includes at least one power source for energizing the heat source, the source of electromagnetic radiation and the controller.

Furthermore, in accordance with a preferred embodiment of the present invention, the apparatus the cavity is a sealed cavity.

Furthermore, in accordance with a preferred embodiment of the present invention, the heat source also provides pulsed light for irradiating the region of skin.

Furthermore, in accordance with a preferred embodiment of the present invention, the pulsed light is broad band pulsed light.

Furthermore, in accordance with a preferred embodiment of the present invention, the heat source is a flash lamp or an arc discharge lamp.

Furthermore, in accordance with a preferred embodiment of the present invention, the flash lamp is a glass xenon lamp.

Furthermore, in accordance with a preferred embodiment of the present invention, the flash lamp is a disposable flash lamp.

Furthermore, in accordance with a preferred embodiment of the present invention, the flash lamp is a quartz xenon lamp and the housing further includes a filter attached to the housing and disposed between the flash lamp and the opening for absorbing a preselected portion of the pulsed broad band light. The absorbed preselected portion includes radiation in the ultra-violet light range which may be harmful to the skin.

Furthermore, in accordance with a preferred embodiment of the present invention, the source of narrow band electromagnetic radiation includes a flash lamp or an arc discharge lamp and a filter attached to the housing and disposed between the flash lamp and the opening for absorbing a preselected portion of the pulsed broad band light, to produce narrow band electromagnetic radiation selectively absorbed by the target tissue.

Furthermore, in accordance with a preferred embodiment of the present invention, the target tissue is blood vessels within psoriatic skin and the source of narrow band electromagnetic radiation emits radiation between the wavelengths of 550 to 610 nanometers.

Furthermore, in accordance with a preferred embodiment of the present invention, the housing further includes a sealing gasket attached to the housing along the circumference of the opening for forming a sealed air cavity disposed between the skin and the heat source.

Furthermore, in accordance with a preferred embodiment of the present invention, The apparatus further includes a cooling unit suitably attached to the housing and controlled by the controller for controllably cooling the skin, to prevent overheating of the skin.

Furthermore, in accordance with a preferred embodiment of the present invention, the cooling unit is activated by the controller when the skin has reached a predetermined temperature after the heat source is energized.

Furthermore, in accordance with a preferred embodiment of the present invention, the apparatus further includes a pump suitably attached to the housing and controlled by the controller for controllably pumping air into the housing to displace the volume of air heated by the heat source with air having a temperature lower than the temperature of the volume of air, to prevent overheating of the skin.

Further yet, in accordance with a preferred embodiment of the present invention, the pump is activated by the controller when the skin has reached a predetermined temperature after the heat source is energized.

Furthermore, in accordance with a preferred embodiment of the present invention, the housing further includes a reflector for reflecting the pulsed broad band light and the narrow band electromagnetic radiation.

Furthermore, in accordance with a preferred embodiment of the present invention, at least part of the housing is coated by a layer of material having a high reflectivity for reflecting the pulsed broad band light and the narrow band electromagnetic radiation.

Furthermore, in accordance with a preferred embodiment of the present invention, The apparatus further includes an extension. The extension has a first end attachable to the opening and a second end placeable on the skin. The extension has an aperture therethrough defining an area for treating the skin.

Furthermore, in accordance with a preferred embodiment of the present invention, the housing is made of a heat insulating material.

Furthermore, in accordance with a preferred embodiment of the present invention, the power source is an electrical power source.

Furthermore, in accordance with a preferred embodiment of the present invention, the power source includes at least one battery, at least one capacitor and an electronic control circuit.

Furthermore, in accordance with a preferred embodiment of the present invention, the power source includes a mains operated direct current supply, at least one capacitor and an electronic control circuit.

Furthermore, in accordance with a preferred embodiment of the present invention, the sensor unit includes at least one optical sensor for sensing the temperature of the skin: the optical sensor receives infra-red radiation emanating from an area of the skin positioned under the housing through an optical element attached within an aperture in the housing. The sensor senses the intensity of the infra-red radiation and provides signals indicative of the intensity to the controller.

Furthermore, in accordance with a preferred embodiment of the present invention, the optical sensor includes an infra-red light sensitive photo-diode.

Furthermore, in accordance with a preferred embodiment of the present invention, the sensor unit includes at least one contact temperature sensor for contacting the skin to sense the temperature of the skin, and for providing the controller with signals indicative of the temperature.

Furthermore, in accordance with a preferred embodiment of the present invention, the contact temperature sensor is a thermistor.

Furthermore, in accordance with a preferred embodiment of the present invention, the apparatus fits into the palm of a hand.

Furthermore, in accordance with a preferred embodiment of the present invention, the controller unit is a programmable controller unit capable of receiving data determining at least one treatment parameter selected from a plurality of treatment parameters for coordinating the timing and the duration of activation of any of the heat source and the source of narrow band electromagnetic radiation.

Furthermore, in accordance with a preferred embodiment of the present invention, the controller unit is a programmable controller unit capable of receiving data determining at least one treatment parameter selected from a plurality of treatment parameters for coordinating the timing and the duration of activation of any of the heat source, the source of narrow band electromagnetic radiation and the pump.

Furthermore, in accordance with a preferred embodiment of the present invention, the programmable controller unit includes a removable storage device on which the plurality of treatment parameters are stored, the removable storage device is capable of being disconnected and removed from the programmable controller for changing the value of at least one of the plurality of treatment parameters prior to reconnecting the storage device to the programmable controller.

Furthermore, in accordance with a preferred embodiment of the present invention, the storage device is selected from a flash memory device, a magnetic bubble memory device, an EPROM memory device, an EEPROM memory device, an optical memory device, an opto-magnetic memory device and a magnetic memory device.

There is further provided, in accordance with a preferred embodiment of the present invention, a method for selective photothermolysis of a target tissue within the skin. The method includes the steps of providing a cavity formed by a housing overlying the skin. The cavity includes a volume of air having a first end proximal to the skin and a second end distal to the skin. The method further includes the step of heating the skin by pulsing a heat source disposed within the cavity to heat the air surrounding the heat source to create a temperature gradient in the volume of air. The temperature gradient has a first temperature at the first end and a second temperature at the second end. The first temperature is lower than the second temperature. The method further includes the step of continuously monitoring the surface temperature of the skin. The method further includes the step of irradiating the skin with a pulse of narrow band electromagnetic radiation when the surface temperature of the skin reaches a first predetermined value. The pulse has a duration sufficient to selectively raise the temperature of the target tissue to the coagulation temperature of the target tissue without coagulating the skin tissue surrounding the target tissue. The method further includes the step of terminating the step of heating of the skin.

Furthermore, in accordance with a preferred embodiment of the present invention, the step of terminating includes manually lifting the housing away from the skin to allow air at room temperature to cool the skin.

Furthermore, in accordance with a preferred embodiment of the present invention, the step of terminating includes the step of activating a cooling unit to cool the skin to prevent overheating of the skin.

Further yet, in accordance with a preferred embodiment of the present invention, the step of terminating includes activating the cooling unit when the surface temperature of the skin reaches a second predetermined value.

Furthermore, in accordance with a preferred embodiment of the present invention, the air cavity is a sealed air cavity disposed between the housing and the skin.

Furthermore, in accordance with a preferred embodiment of the present invention, the heat source is a flash lamp or a gas discharge lamp and the step of heating further includes the step of additionally heating the skin by irradiating the skin with broad band incoherent radiation produced by the flash lamp or gas discharge lamp.

Furthermore, in accordance with a preferred embodiment of the present invention, the step of additionally heating further includes the step of filtering the broad band incoherent radiation, prior to irradiating the skin therewith, to remove a preselected portion thereof. The preselected portion includes radiation in the ultra-violet light range which may be harmful to the skin.

Furthermore, in accordance with a preferred embodiment of the present invention, the first predetermined value is between 55° C. and 65° C., and the coagulation temperature is between 70° C. and 90° C.

Furthermore, in accordance with a preferred embodiment of the present invention, the step of terminating includes automatically pumping a coolant into the cavity of the housing when the surface temperature of the skin reaches a second predetermined value.

Furthermore, in accordance with a preferred embodiment of the present invention, the step of terminating includes automatically pumping air at a temperature lower than the temperature of the surface of the skin into the cavity of the housing when the surface temperature of the skin reaches a second predetermined value.

Finally, in accordance with a preferred embodiment of the present invention, the target tissue is blood vessels and the skin is psoriatic skin and the pulse of narrow band electromagnetic radiation includes radiation between the wavelengths of 550 to 610 nanometers.

BRIEF DESCRIPTION OF THE DRAWINGS

The invention is herein described, by way of example only, with reference to the accompanying drawings, in which like components are referred to by like reference numerals wherein.

DETAILED DESCRIPTION OF THE PREFERRED EMBODIMENTS

The present invention is of a method and device for selective photothermolysis of relatively large surgical targets. Specifically, the present invention can be used to remove varicose veins and similar diseased or unsightly tissue with minimal damage to the surrounding healthy tissue. The present invention can also be used for treatment of psoriasis.

The principles and operation of a method and device for selective photothermolysis according to the present invention may be better understood with reference to the drawings and the accompanying description.

Figure 1:
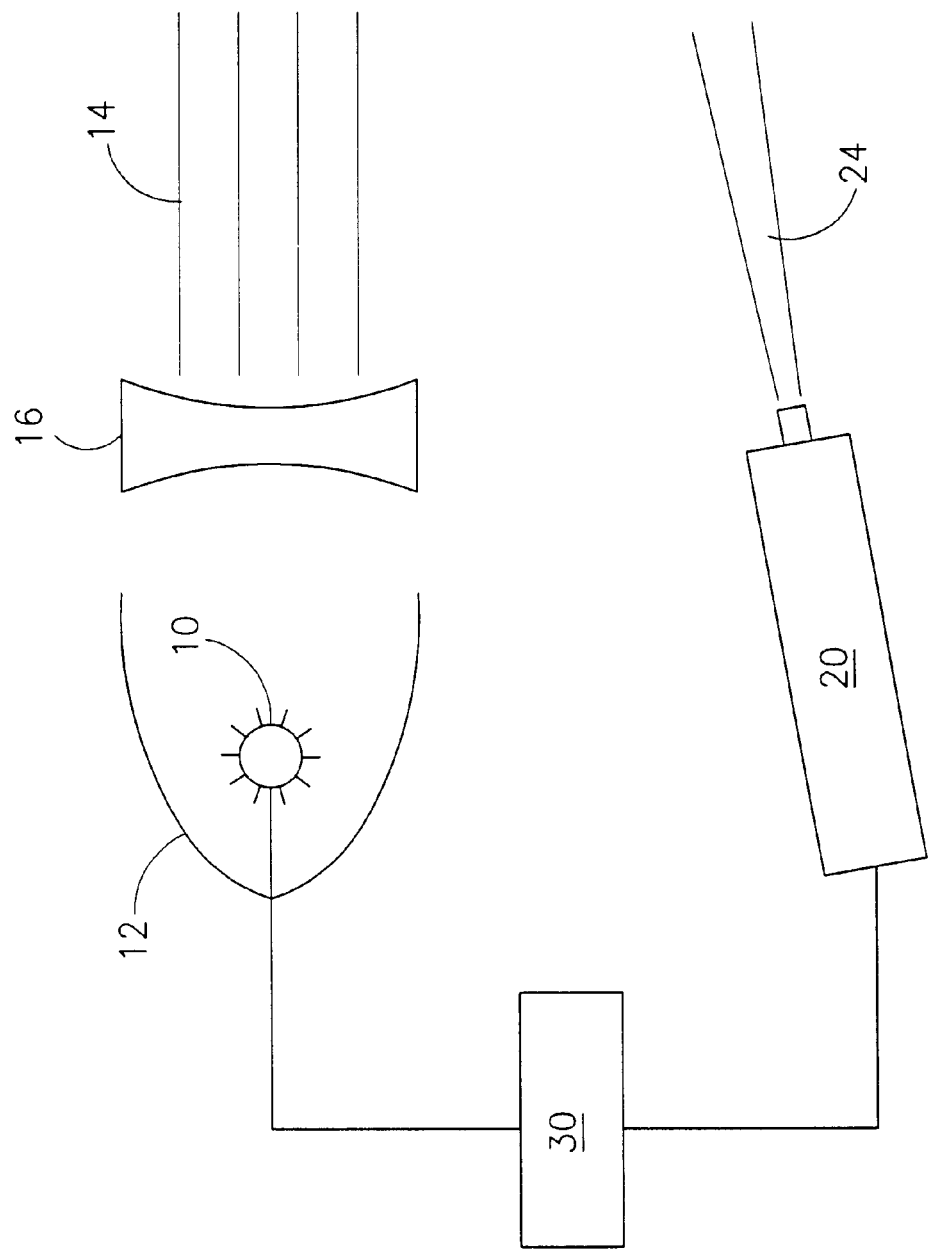
FIG. 1 is a schematic diagram of a preferred embodiment of the device of the present invention in which the source of monochromatic light is a laser.

Referring now to the drawings, FIG. 1 is a schematic diagram of a preferred embodiment of the device of the present invention. A high intensity lamp 10 functions as a source of broad-band (white) light 14. Because lamp 10 emits light in all directions, a parabolic reflector 12 and a concave lens 16 are provided to collimate broad-band light 14, so that substantially all of the energy emitted by lamp 10 is directed at the target and the surrounding tissue. A laser 20 emits substantially monochromatic light 24, preferably at a wavelength of 585 nanometers, also towards the target and the surrounding tissue. A control system 30 supplies power to lamp 10 and laser 20, and also turns lamp 10 and laser 20 on and off in accordance with the pulse schedule shown in FIG. 2.

Preferably, lamp 10 is a xenon arc lamp. Preferably, laser 20 is a flash lamp-pulsed dye laser, for example the ScleroLASER manufactured by Candela Corporation of Wayland Mass.

Figure 2:
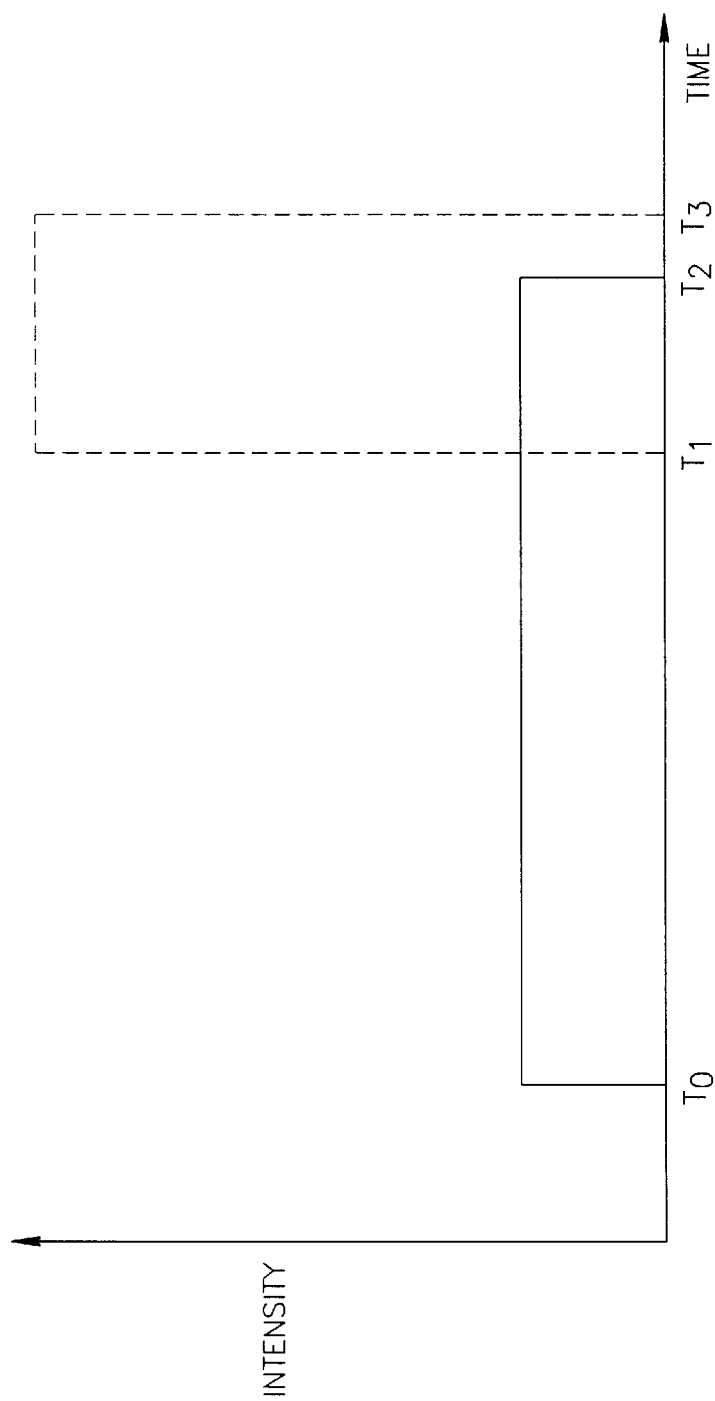
FIG. 2 shows a pulse schedule for the device of FIG. 1.

FIG. 2 shows a pulse schedule for the device of FIG. 1. The solid line in FIG. 2 represents the duration and intensity of a pulse of broad-band light 14. The dashed line in FIG. 2 represents the duration and intensity of a pulse of monochromatic light 24. Broad-band light 14 is turned on at time $T_0$ and is kept on long enough, until time $T_2$, to heat the target and the surrounding tissue to about 60° C. As the temperature of the surrounding tissue approaches the desired final value, monochromatic light 24 is turned on at time $T_1$, and is kept on until time $T_3$, long enough to cause coagulation of the target but not long enough to damage the surrounding tissue. Preferably, the duration of the monochromatic pulse is between about 0.1 milliseconds and about 10 milliseconds.

Figure 3:
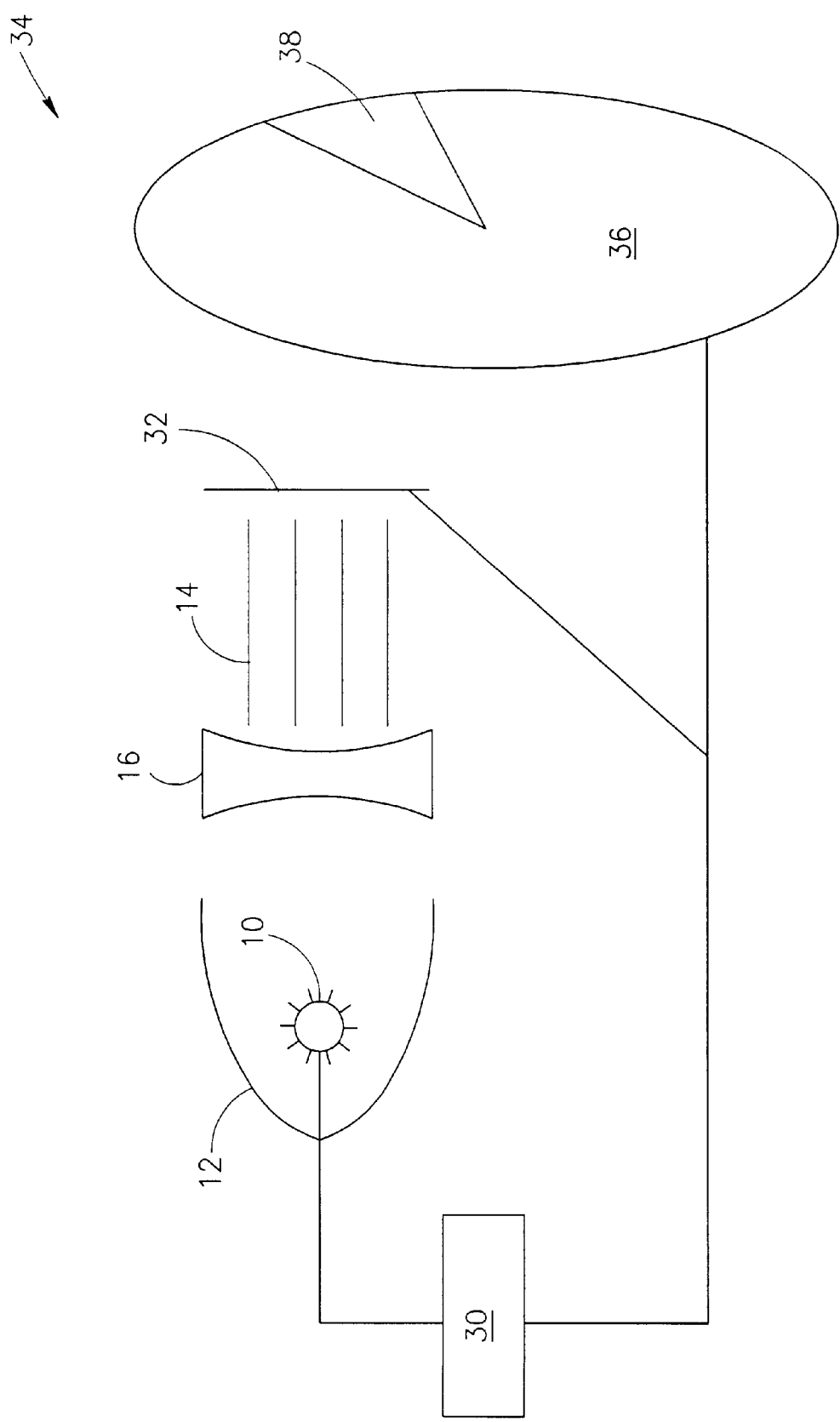
FIG. 3 is a schematic diagram of a preferred embodiment of the device of the present invention in which the source of monochromatic light is the same as the source of the broad-band light.

FIG. 3 is a schematic diagram of another preferred embodiment of the device of the present invention. In this embodiment, lamp 10 serves as the source of both the broad-band radiation and the monochromatic radiation that are incident on the target and the surrounding tissue. In this embodiment, a mechanical shutter 32 serves to alternately block and pass broad-band light 14, thus causing the light emerging from the device to be pulsed. A rotating circular filter 34 having two sections, a white section 36 and a colored section 38, serves to filter the broad-band pulses passed by shutter 32. White section 36 attenuates all wavelengths to substantially the same degree, thereby providing a broad-band pulse of the proper intensity and duration to heat the target and the surrounding tissue to about 60° C. Colored section 38 attenuates all but a narrow spectral band of light centered on a wavelength of 585 nanometers. Control system 30 synchronizes the movement of shutter 32 and filter 34 to provide light pulses according to the pulse schedule of FIG. 4.

Note that lamp 10 must be much more powerful in the embodiment of FIG. 3 than in the embodiment of FIG. 1, because in the embodiment of FIG. 3, lamp 10 must provide enough spectral power in the vicinity of 585 nanometers to coagulate the target. It is for this reason that white section 36 of filter 34 is required in this embodiment.

Figure 4:
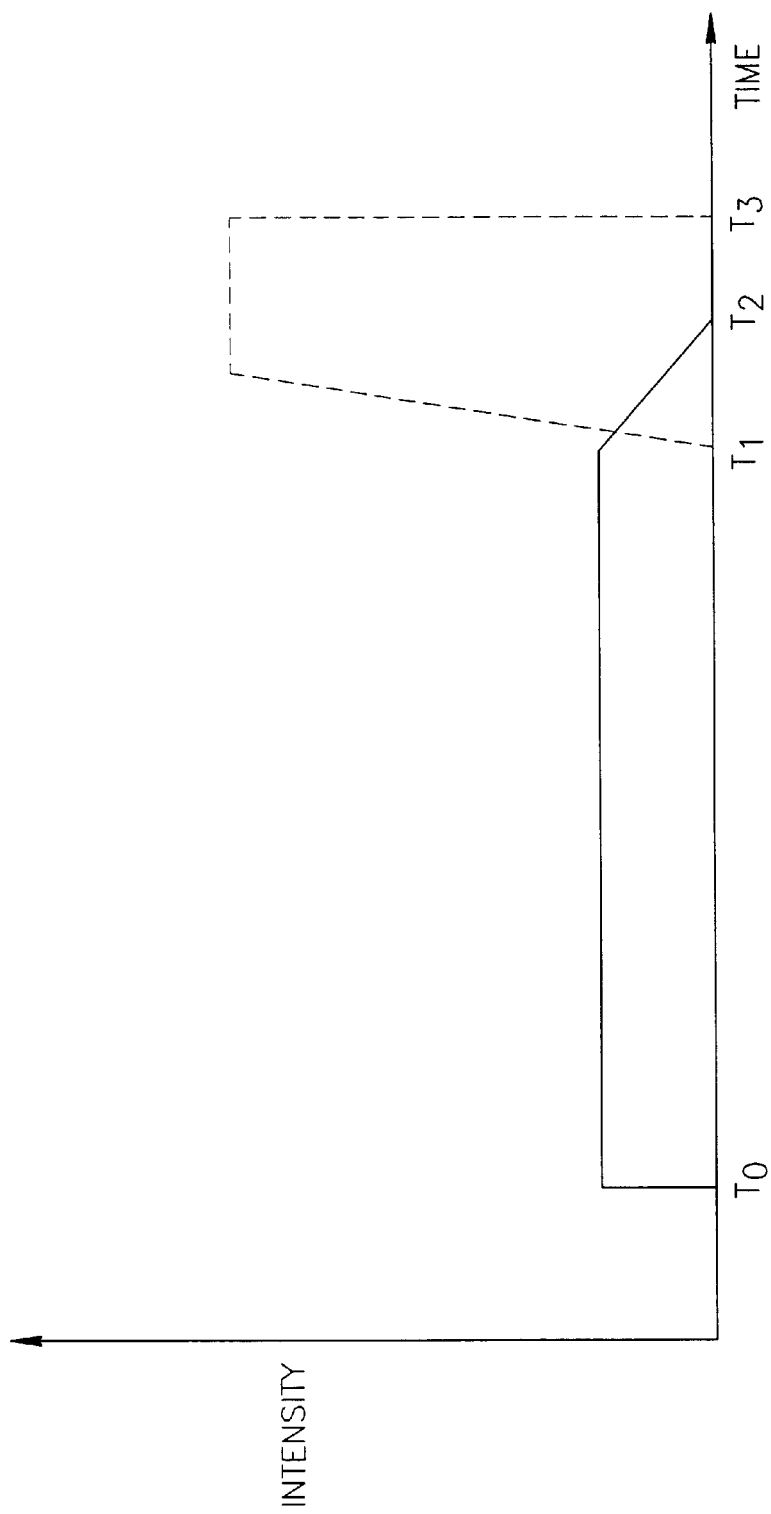
FIG. 4 shows a pulse schedule for the device of FIG. 3.

FIG. 4 shows a pulse schedule for the device of FIG. 3. As in FIG. 2, a solid line represents a broad-band pulse and a dashed line represents a monochromatic pulse. At time $T_0$, with filter 34 positioned so that white section 36 is in the optical path of broad-band light 14, shutter 32 is opened, allowing broad-band light 14 to pass through, and to be attenuated by, white section 36. Filter 34 is rotated, until, at time $T_1$, colored section 38 begins to intercept broad-band light 14. At time $T_2$, all of broad-band light 14 is passing through colored section 38, so that the light emerging from the device is substantially monochromatic. At time $T_3$, shutter 32 is closed, terminating the monochromatic pulse.

Figure 5:
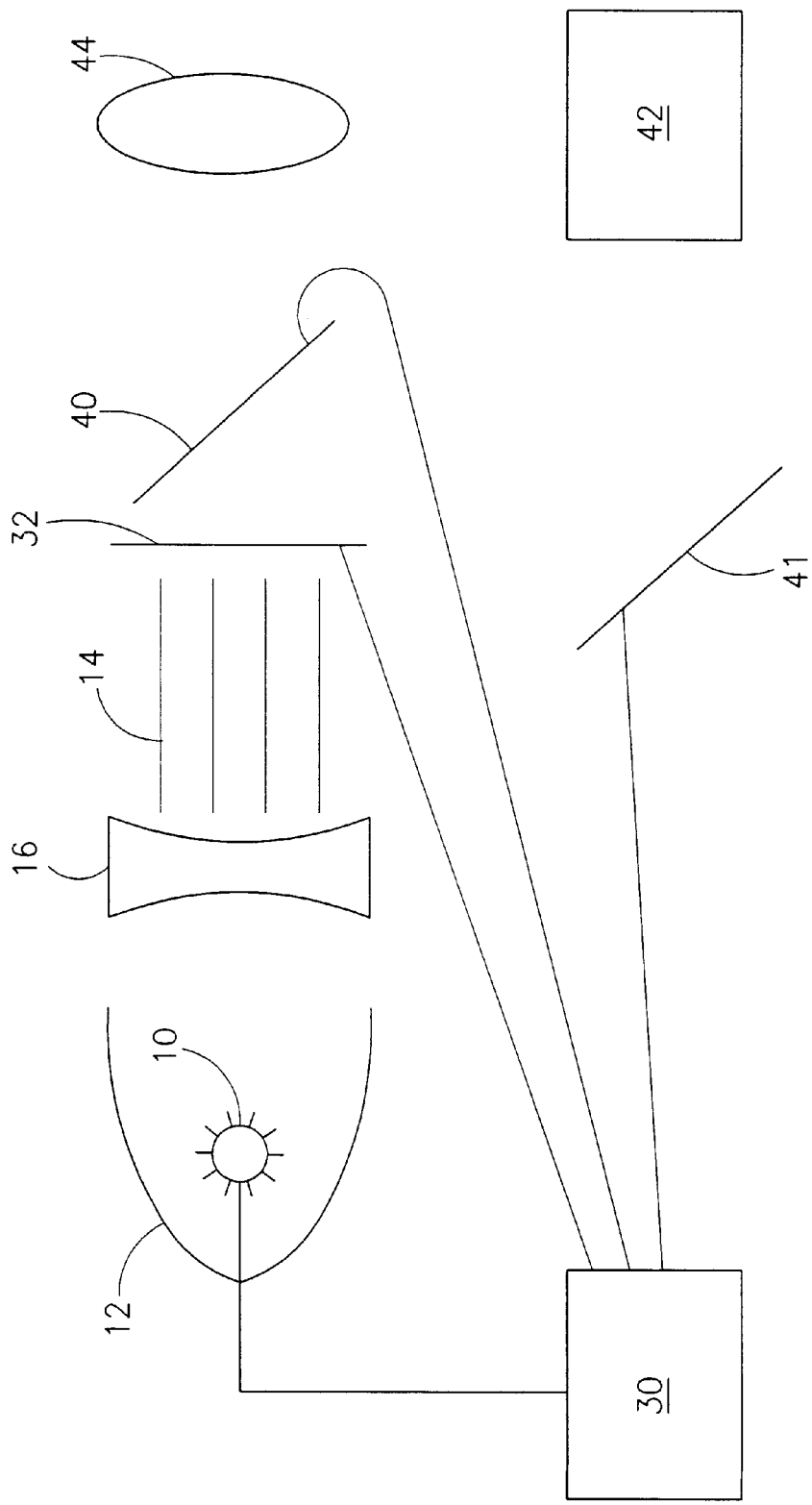
FIG. 5 show an alternative embodiment of the device of FIG. 4.
Figure 6:
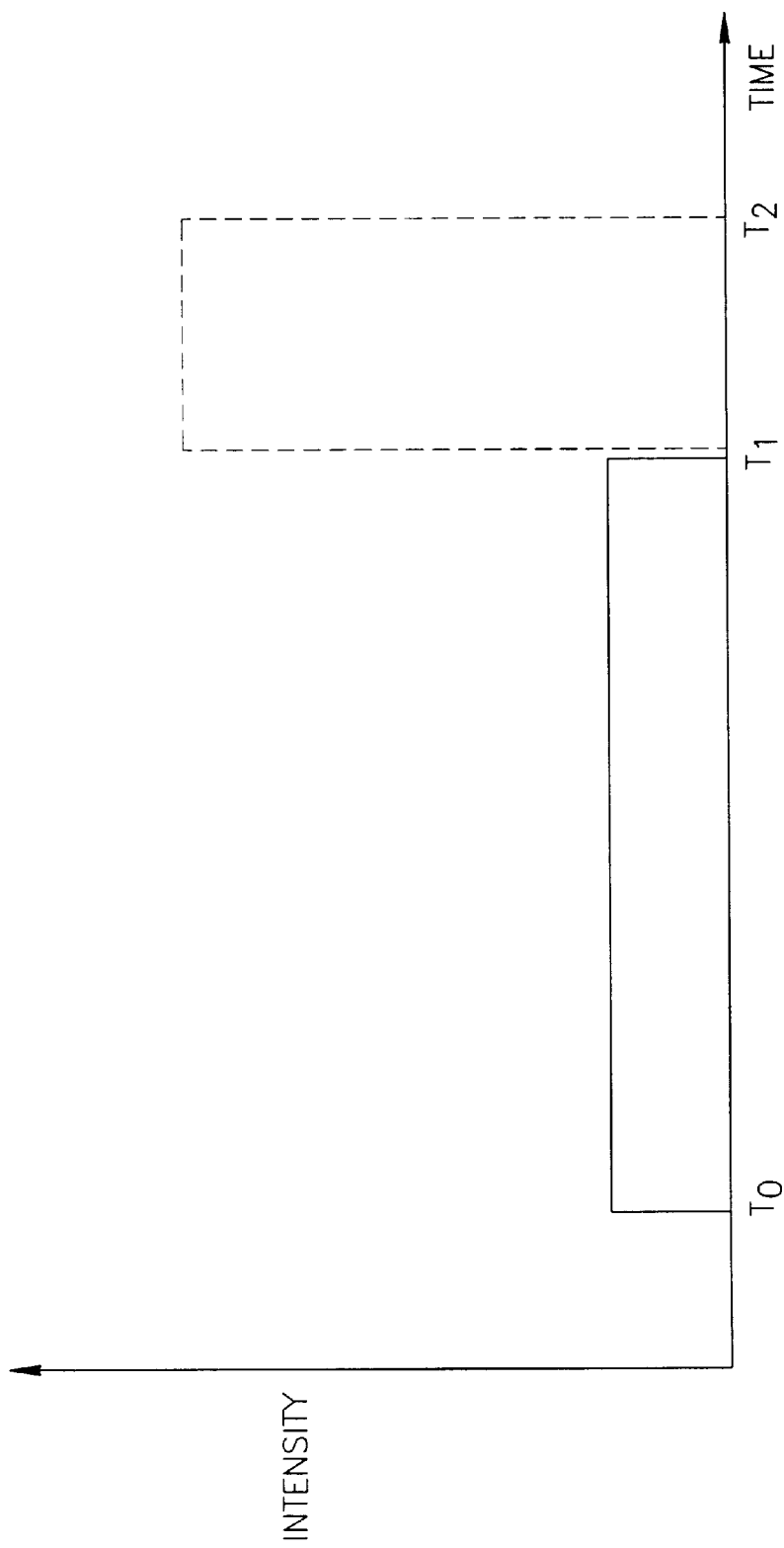
FIG. 6 shows a pulse schedule for the device of FIG. 5.

FIG. 5 is a schematic diagram of a variant of the device of FIG. 3. In the device of FIG. 5, a movable mirror 40 is provided to deflect light passed by shutter 32 to a fixed mirror 41 and a monochromator 42. The device of FIG. 5 generates pulses according to the pulse schedule of FIG. 6, in which, again, the solid line represents a broad-band pulse and the dashed line represents a monochromatic pulse. At time $T_0$, with mirror 40 withdrawn, shutter 32 is opened, allowing broad-band light 14 to pass through an attenuation filter 44 and thence to the target and the surrounding tissue. Like white region 36 of filter 34, attenuation filter 44 attenuates all wavelengths to substantially the same degree, to provide a broad-band pulse of the proper duration and intensity to heat the target and the surrounding tissue to about 60° C. At time $T_1$, mirror 40 is moved into place, terminating the broad-band pulse, and, deflecting broad-band light 14 so that it passes, via mirror 41, through monochromator 42, thereby initiating the monochromatic pulse. Thus, the monochromatic pulse starts substantially immediately after the termination of the broad-band pulse. Monochromator 42 passes on to the target only a narrow spectral band of light centered on a wavelength of 585 nanometers. At time $T_2$, shutter 32 closes, terminating the monochromatic pulse.

Additional embodiments of the present invention may be constructed for treating varicose veins and psoriasis skin at considerably less expense than that associated with presently known methods.

Figure 7:
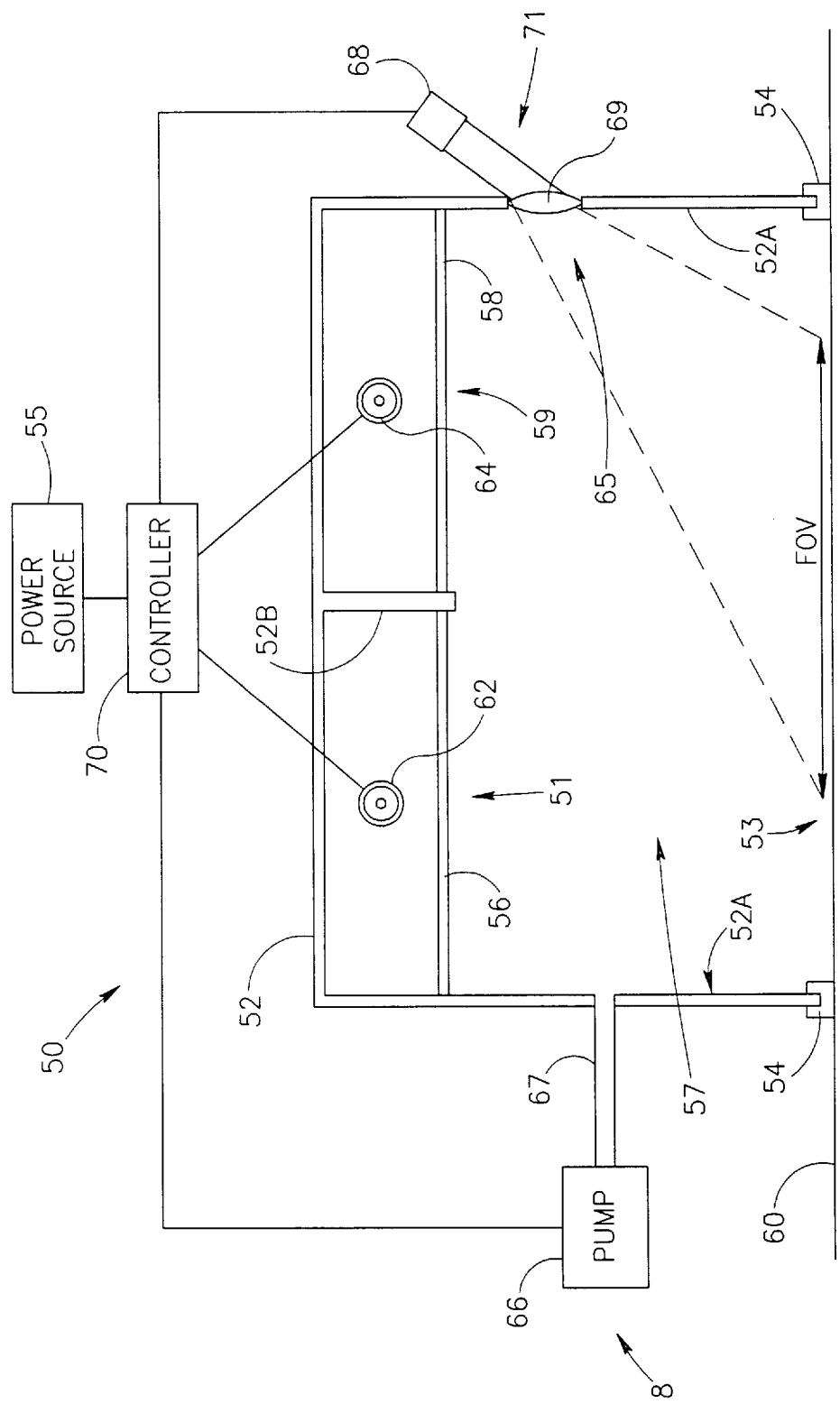
FIG. 7 is a schematic cross sectional view illustrating apparatus for selective photothermolysis, having a heat source and a source of narrow band electromagnetic radiation, in accordance with another preferred embodiment of the device of the present invention.

Reference is now made to FIG. 7 which is a schematic cross sectional view illustrating an apparatus 50 for selective photothermolysis, having a heat source and a source of narrow band electromagnetic radiation, in accordance with another preferred embodiment of the device of the present invention The apparatus 50 includes a housing 52 made of a thermally insulating material such as high temperature plastic a ceramic material or any other suitable thermally insulating material. The housing 52 has an opening 53 which can be placed on the surface of the tissue to be treated, for example, on the surface of the skin 60. The inner surface 52A of the housing 52 is coated with a diffusely reflective coating of near-perfect reflectivity, such as finely divided titanium dioxide. Alternatively, a suitably shaped reflector (not shown) may be attached to the housing 52 for reflecting electromagnetic radiation produced within the housing as disclosed in detail hereinbelow, towards the skin 60.

The apparatus 50 includes a sealing gasket 54 made from soft rubber or the like for sealing the contact with the skin 60 when the opening 53 of apparatus 50 is placed on the skin 60. When the housing 52 is lightly pressed onto the skin 60, a sealed cavity 57 is formed. The sealed cavity 57 includes a volume of air (not shown) which is enclosed between the skin 60 and the housing 52.

The upper part of the housing 52 includes a heat source 51 and a source of narrow band electromagnetic radiation 59. A separator 52B extending from the housing 52 separates the heat source 51 from the source of radiation 59. The heat source 51 and the source of radiation 59 may be rectangular or ellipsoidal in cross section or may have any other suitable cross section or shape. The heat source 51 includes a lamp 62 attached to the housing 52, and a filter 56 attached to the housing 52 and to the separator 52B.

The lamp 62 may be any suitable flash lamp or gas discharge arc lamp such as the quartz-xenon flash lamp model G5109, commercially available from The Electronic Goldmine, Ariz., U.S.A. The filter 56 may be any filter suitable for filtering the harmful ultra violet radiation which is produced by the flash lamp 62 while passing through the non-harmful portion of the broad band radiation produced by pulsing the flash lamp 62. For example, the filter 56 may be the long wave pass filter model 450FH90-25, commercially available from Andover Corporation, N.H., U.S.A. Thus, the filter 56 blocks ultraviolet light, from the lamp 62, from reaching the skin 60.

The source of radiation 59 includes a lamp 64 attached to the housing 52 and a filter 58 attached to the housing 52 and to the separator 52B. The lamp 64 may be any suitable flash lamp or gas discharge arc lamp such as the quartz-xenon flash lamp model G5109, commercially available from The Electronic Goldmine, Ariz., U.S.A. The filter 58 is any suitable band pass filter which absorbs a substantial part of the electromagnetic radiation produced by the lamp 64 while passing therethrough only a suitable narrow band of the electromagnetic radiation which is selectively absorbed by the target tissue. For example, for the treatment of psoriatic skin, the target tissue is the blood vessels within the skin, therefore the filter 64 should selectively pass a narrow band of radiation around the absorption maximum of oxyhemoglobin.

Preferably, filter 58 includes a combination of two filters, a visible long wave pass filter such as model 550FH90-25 filter, and the near infrared short wave pass filter model 600FL07-25 which are commercially available from Andover Corporation. This filter combination passes only wavelengths in the range 550 to 600 nanometers. It is noted that, other suitable narrow band filters or filter combinations may also be used provided that they transmit the required narrow band radiation which can be selectively absorbed by the target tissue without being substantially absorbed by the tissue surrounding the target tissue.

It is noted that, the use of an Interference filter in the apparatus of the present invention is not recommended because the light from flash lamp 64 is spread at a large angle of incidence on the filter.

The apparatus 50 further includes a cooling unit 8 which includes a pump 66 connected to the housing 52 by a suitable tube 67 for pumping air into the sealed cavity 57.

It is noted that while the cooling unit 8 of the apparatus 50 includes a pump 66, other embodiments of the present invention may include other types of cooling devices as is disclosed in detail hereinafter.

The apparatus 50 further includes a sensing unit 71 attached to the housing 52. The sensing unit 71 includes a sensor 68 and a collimating optical element 69. The optical element 69 is attached within an aperture 65 in the housing 52. The optical element 69 and the optical sensor 68 are aligned such that the field of view of the sensor unit 71 represented by the double headed arrow labeled FOV, covers a substantial portion of the skin under the opening 53 but does not include any part of the housing 52.

Preferably, the sensing unit 71 is an infra-red (IR) sensing unit such as the model A 53,367 Infrared thermometer, commercially available from Edmund Scientific Company, N.J., U.S.A. However, any other suitable optical sensing unit can be used provided that it has sufficient sensitivity in the relevant range of temperatures (roughly 30°–80° C.). The lens 69 is an infra-red lens substantially transparent to infra-red radiation.

It is noted that, while in the preferred embodiment of the invention illustrated in FIG. 7 the optical element is a collimating infra-red lens 69, other preferred embodiments of the present invention may be constructed that include other optical elements such as an optical window, a holographic lens, a composite lens, a micro-lens array or any other optical element suitable for collimating infra red radiation in the spectral band necessary for sensing of the temperature of the skin surface within the field of view FOV.

It is further noted that, while the preferred embodiment of the invention illustrated in FIG. 7 has only one sensing unit 71 including one optical sensor 68, other preferred embodiments of the present invention may be constructed that include more than one optical unit. This may be required to include a wider portion of the surface of the skin 60 or for other alignment and or other manufacturing considerations. In such a case, additional apertures are made within the housing 52.

The apparatus 50 also includes a controller 70 and a power source 55. The power source 55 is suitably connected to the controller 70 for providing power to the controller 70. The controller 70 is suitably connected to the lamps 62 and 64 for controlling the energizing thereof. The controller 70 is also connected to the sensing unit 71 for receiving signals therefrom, the signals representing the temperature of the surface of the portion of the skin 60 which is included in the field of view FOV. The controller 70 is also connected to the pump 66 for controlling the operation thereof.

The power source 55 is, preferably, an electrical power source such as a DC power supply connectable to a mains AC power socket, but can also be one or more disposable batteries, one or more rechargeable batteries, or any other suitable electrical power source.

Additionally, the power source 55 may be included within the controller 70 or may be comprised of a plurality of power sources (not shown) each capable of providing different voltage and/or current levels. For example, one power source (not shown) may be used for powering the controller 70 while another power source capable of delivering higher current densities may be used for energizing the lamps 62 and 64, and the pump 66.

To use the apparatus 50 of FIG. 7, the user places opening 53 adjacent to the skin 60 to be treated and lightly presses against the skin to achieve sealing of the air volume within the cavity 57 by the sealing gasket 54. The user then activates the treatment sequence by pressing a button or a suitable switch (not shown) and the controller 70 activates the flash lamp 62, producing a pulse of 1 to 3 milliseconds duration that irradiates the skin tissue with broad band light having an energy density of approximately 0.5 to 5 Joule/$cm^2$. The filter 56 filters out most of the radiation within the ultra-violet range, preventing it from reaching the skin 60. The skin tissue under the opening 53 and the target therewithin are thus heated to a temperature which is below the tissue coagulation temperature. Immediately after the pulse, the flash-lamp 62 reaches a temperature of approximately 600° C. to 800° C. The exact temperature of the flash lamp 62 depends, inter alia, on the type of flash lamp chosen, the operating voltage and the current flowing through the flash lamp. The flash lamp 62 heats the air surrounding it and the filter 56, and creates a temperature gradient in the volume of air enclosed within the sealed cavity 57, forcing heat to flow along the gradient into the skin 60 and further heating the skin 60 and target (not shown).

The optical sensor 68 senses the intensity of infra-red radiation emitted from the skin 60 within the field of view FOV and sends signals to the controller 70, which processes the signals to determine the temperature of the skin 60 within the field of view FOV. When the temperature of the skin 60 within the field of view FOV reaches a certain predetermined temperature, preferably about 65° C., the controller 70 activates the flash lamp 64, producing a pulse having a duration of approximately 0.5 to 5 milliseconds, irradiating the target with narrow band light having a power density of 0.75 to 3.0 Joule/$cm^2$. The narrow band radiation is selectively absorbed by the target tissue, for example, the blood vessels and capillaries (not shown) within the psoriatic skin, thus selectively heating and coagulating the blood vessels and capillaries without damaging the surrounding skin tissue.

Almost all of the energy from the flash lamps 62 and 64 that passes the filters 56 and 58 heats the skin and the capillaries therein Because the inner surface 52A of the housing 52 is almost perfectly reflective, and because the housing 52 is thermally insulating.

After the coagulation of the blood vessels and capillaries is achieved the controller 70 activates the pump 50 which pumps air at room temperature into the cavity 53 of the housing 52 through the tube 67 in order to cool the skin 60 and to prevent the skin 60 from reaching the temperature of coagulation due to the continued heat conduction along the temperature gradient within the volume of air enclosed within the cavity 57. The controller 70 activates the pump 66 when the temperature of the skin 60, determined by the controller 70 from the signals of the optical sensor 68, reaches a predetermined temperature value. The rate of pumping of relatively cold air by the pump 60 is high enough to cool the skin 60 fast enough so as to prevent burns or coagulation of the skin 60. Alternatively, the controller 70 may activate the pump 66 at the termination time of the narrow band light pulse of flash-lamp 64. The time of the activation of the pump 66 by the controller 70 may also be done at a predetermined time after the termination of the narrow band light pulse of flash-lamp 64. This time of pump activation may be determined empirically.

It is noted that, the apparatus 50 should have an opening 53 which is of a sufficient area in order to increase the ratio between the heated volume to the surface thus decreasing the loss of heat to the surrounding tissue and increasing the optical coupling to the target tissue.

Figure 8:
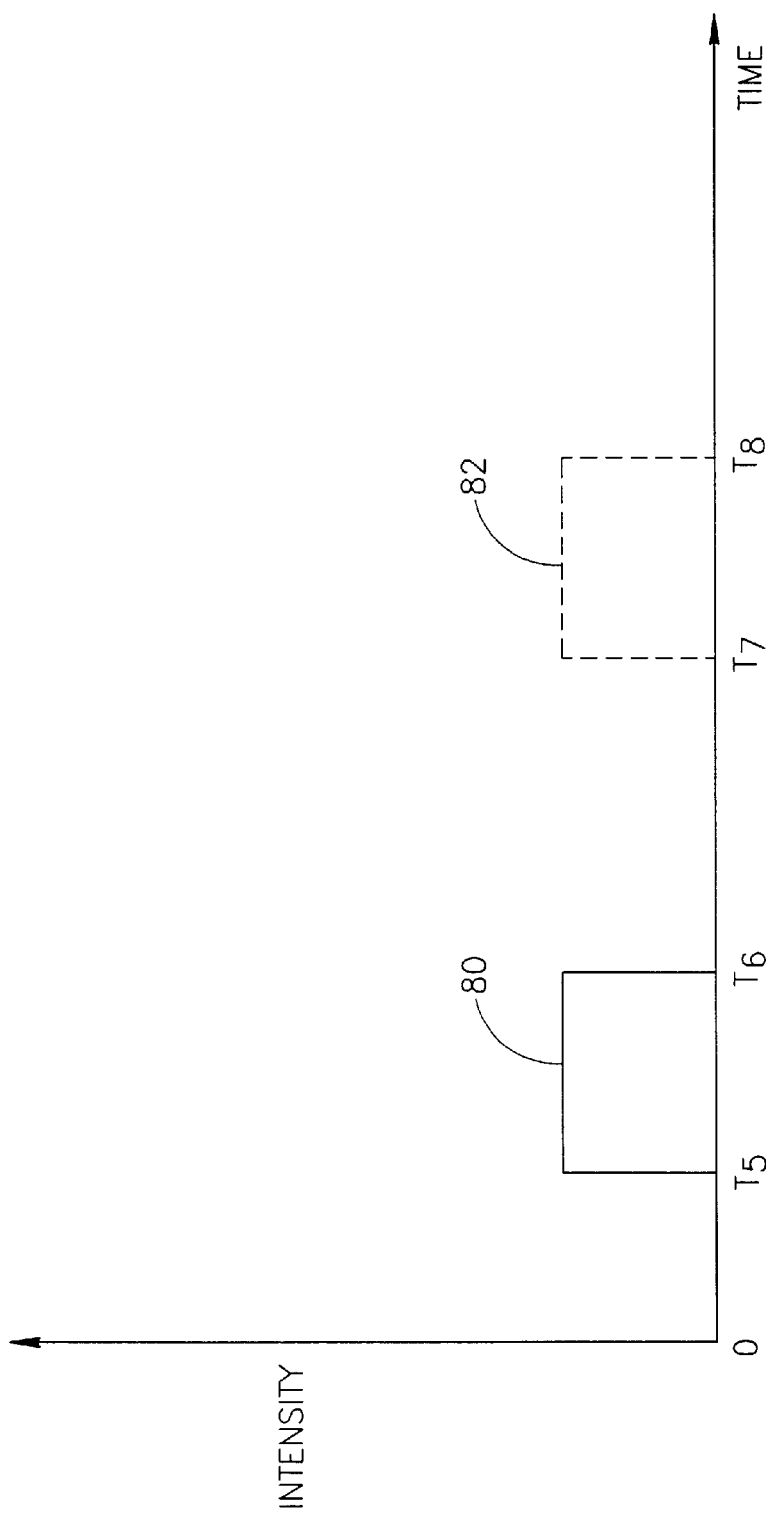
FIG. 8 Is a schematic diagram illustrating a pulse schedule for the device of FIG. 7.

Reference is now made to FIG. 8 which is a schematic diagram illustrating a pulse schedule for the device of FIG. 7;

The vertical axis of FIG. 8 represents the arbitrary pulse intensity and the horizontal axis represents time. The solid line curve 80 represents the duration and intensity of the first pulse of broad band radiation of flash lamp 62. The dashed line curve 82 represents the duration and intensity of the pulse of narrow band radiation of the flash lamp 64. The flash lamp 62 is turned on at time $T_5$, and is kept on until time $T_6$ to heat the target and the surrounding skin tissue above normal body temperature. At the time $T_6$ the flash lamp 62 is turned off and heat flows from the flash lamp 62 and the filter 56 towards the skin 60.

As the temperature of the target tissue and the surrounding tissue approaches the desired final value of about 65° C., the flash lamp 64 is turned on at time $T_7$, and is kept on until time $T_8$, producing a pulse of narrow band radiation which irradiates the skin 60 for a duration sufficient to cause coagulation of the target tissue without substantially damaging the surrounding tissue of the skin 60. Preferably, the duration of the narrow band radiation pulse is in the range of approximately 0.5 to 5 milliseconds.

In accordance with one preferred embodiment of the present invention, the controller 70 activates the pump 66 at the time $T_8$ to pump fresh air at room temperature into the housing 52 in order to prevent the skin from reaching the temperature of coagulation.

In accordance with another preferred embodiment of the present invention, the controller 70 activates the pump 66 when the temperature of the skin 60, sensed by the sensing unit 71 reaches a predetermined value.

Preferably, this predetermined temperature value is in the range of approximately 70°–75° C. However, the predetermined temperature value may somewhat vary depending, inter alia, on the rate of rise of the skin temperature and of the attainable efficiency of the cooling of the skin by the cooling unit such as the pump 66.

It is noted that, while the apparatus 50 of FIG. 7 includes a quartz-xenon lamp which has an extended useful lifetime, it is also possible to use glass-xenon flash lamps or other types of gas arc discharge lamps which do not emit high intensities of UV light. The use of such lamps may obviate the need for a UV filter such as the filter 56 of FIG. 7.

Figure 9:
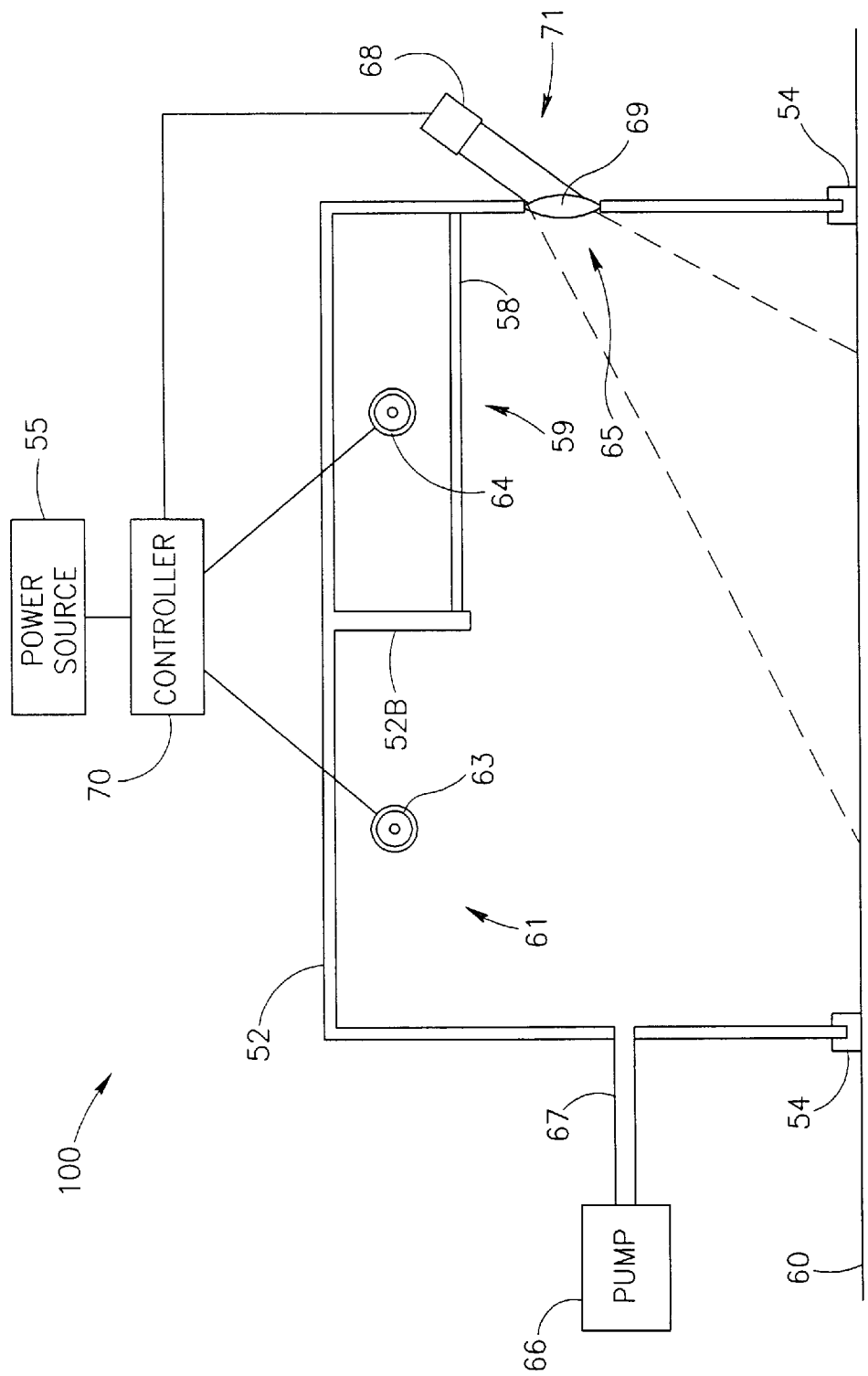
FIG. 9 is a schematic cross sectional view illustrating apparatus for selective photothermolysis, including a glass-xenon flash lamp, in accordance with yet another preferred embodiment of the device of the present invention.

Reference is now made to FIG. 9 which is a schematic cross sectional view illustrating apparatus for selective photothermolysis, including a glass-xenon flash lamp, in accordance with yet another preferred embodiment of the present invention. The apparatus 100 is similar to the apparatus 50 of FIG. 7 except that instead of the heat source 51 of FIG. 7, the apparatus 100 includes a heat source 61 which comprises a glass-xenon flash lamp 63 such as model A1033 glass-xenon flash lamp, commercially available from The Electronic Goldmine, Ariz., U.S.A., or any other suitable flash lamp or gas discharge lamp that does not emit substantial energy in the ultraviolet range harmful to living tissue. The heat source 61 does not need to include a UV filter because the glass envelope of the flash lamp 63 absorbs most of the harmful UV radiation emitted in the arc discharge.

It will be appreciated by those skilled in the art that, it is possible to replace the sensing unit 71 of FIG. 7 by other sensing units which are not optical sensing units.

Figure 10:
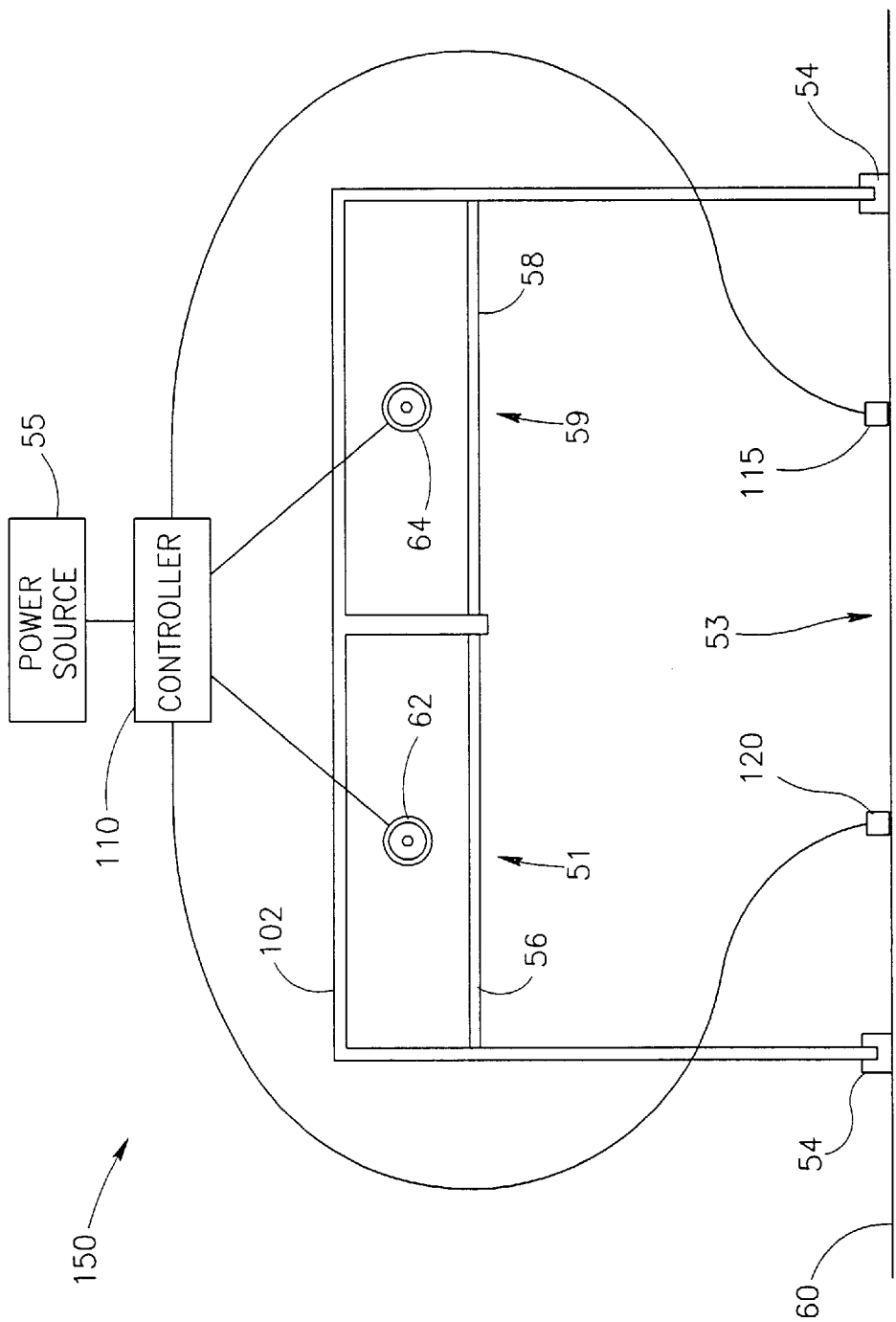
FIG. 10 is a schematic cross sectional view illustrating apparatus for selective photothermolysis, having contact temperature sensors, in accordance with yet another preferred embodiment of the device of the present invention.

Reference is now made to FIG. 10 which is a schematic cross sectional view illustrating an apparatus 150 for selective photothermolysis, having contact temperature sensors, in accordance with yet another preferred embodiment of the present invention. The apparatus 150 includes a housing 102 which is similar to the housing 52 of FIG. 7, except that it does not include an aperture such as the aperture 65 of the housing 52 of FIG. 7, therewithin. Furthermore, in contrast to the apparatuses 50 and 100 of FIGS. 7 and 9, respectively, which include a pump 55, the apparatus 150 does not include a pump. The apparatus 150 also includes a controller 110 and two contact temperature sensors 115 and 120 which are suitably connected to the controller 110. The apparatus 150 further includes a power source 55 suitably connected to the controller 110.

The apparatus 150 also includes flash lamps 62 and 64, filters 56 and 58, and sealing gasket 54 as illustrated in FIG. 7 and disclosed in detail for apparatus 50 hereinabove.

The method of operation of the apparatus 150 of FIG. 10 is somewhat different from that of the apparatuses 50 and 100 disclosed hereinabove. The manner and the sequence of operating the heat source 51 and the narrow band radiation source 59 is similar to that disclosed in detail for the apparatus 50 of FIG. 7 hereinabove. However, in contrast with the optical sensing of temperature in the apparatuses 50 and 100 of FIGS. 7 and 9, respectively, the sensing of the temperature of the skin 60 is performed in the apparatus 150 by the two contact sensors 115 and 120 which are placed in contact with the skin 60 as the apparatus 110 is placed in contact with the skin 60. The contact sensors 115 and 120 generate signals representing the temperature of the skin 60 at the contact point of the contact sensors 115 and 120 with the skin 60. The signals are received by the controller 110 which processes the signals to determine the temperature of the skin 60 therefrom.

Similar to the method of use of the apparatus 50, when the averaged temperature of the of the skin tissue, as determined by the controller 110 from the signals received from the sensors 115 and 120, approaches the temperature value of about 65° C. after the activation of the flash lamp 62 by the controller 110, the flash lamp 64 is turned on by the controller 110 to produce a pulse of narrow band radiation as disclosed hereinabove. However, in contrast to the method of use of the apparatus 50, the user of the apparatus 150 terminates the heating of the skin 60 after the coagulation of the target tissue (not shown) by manually lifting the apparatus 150 off the skin 60 to enable air at room temperature to reach the skin 60 and gradually cool it.

It is noted that, while the apparatus 150 of FIG. 10 includes two contact sensors 115 and 120 for determining an average temperature of the skin 60, other preferred embodiments of the present invention can be constructed in which a single contact sensor is used to monitor the temperature of the skin at a single contact point (not shown). Alternatively, many contact sensors may also be used for obtaining a better average of the temperature of the skin.

It is further noted that in the cases where multiple contact sensors are used, the analog signals of all the sensors may be averaged prior to being further processed by the controller 110 in order to simplify the determination of the averaged skin temperature.

It is still further noted that, the contact temperature sensors 115 and 120 must have a fast response time so as to sense the temperature of the surface of the skin 60 fast enough as the temperature of the skin rises to enable the controller 110 to timely activate the pulse 82 (FIG. 8) and/or the cooling unit 8 (FIG. 7). This can be achieved by using thermistors or other suitable temperature contact sensors having a minimal thermal mass.

It is further noted that various methods for determining the temperature of a surface using optical Infra-red sensors or one or more contact sensors are well known in the art. Such methods are not included in the subject matter of the present invention and will therefore not be described herein in detail.

Figure 11:
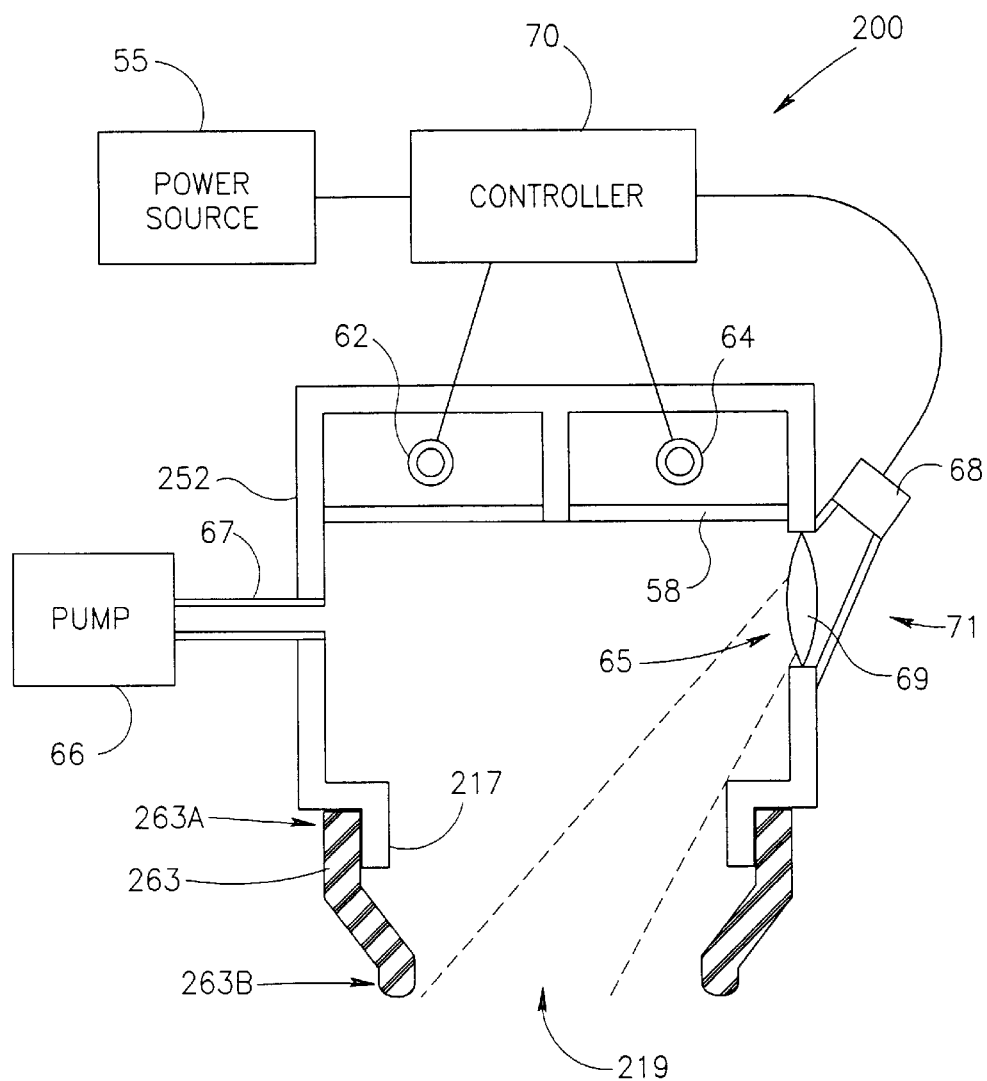
FIG. 11 is a schematic cross section illustrating an apparatus for selective photothermolysis adapted for use with a plurality of differently shaped extenders, in accordance with yet another preferred embodiment of the present invention.

Reference is now made to FIG. 11 which is a schematic cross section illustrating an apparatus for selective photothermolysis adopted for use with a plurality of differently shaped extenders, in accordance with yet another preferred embodiment of the present invention. In contrast to the apparatus 50 of FIG. 7, the apparatus 200 of FIG. 11 includes a housing 252 having a raised collar 217.

The apparatus 200 further includes flash lamps 62 and 64, filters 56 and 58, a controller 70 and a power source 55, a pump 66 and a tube 67, and a sensing unit 71 constructed and operative as disclosed in detail hereinabove for the apparatus 50 of FIG. 7. The apparatus 200 further includes an extender 263 which is detachably attached to the housing 252. The attaching of the extender 263 to the housing 252 is performed by forcing the extender 263 over the raised collar 217.

The extender 263 is a hollow extender having a first end 263A attachable to the raised collar 217 and a second end 263B for contacting the skin (not shown). The extender 263 has an aperture 219 therethrough defining an area for treating the skin. In one preferred embodiment, the extender 263 is a metal extender. However, the extender 263 may also be made of a thermally insulating material such as a plastic or a ceramic material. The apparatus 200 is operated by pressing the aperture 219 against the skin (not shown) and operating the apparatus for treating the skin as disclosed for the apparatus 50 of FIG. 7 hereinabove.

It is noted that, many different forms of the extender 263 can be made, each having an aperture of a different shape and/or size for adapting the apparatus 200 to be used for photothermolytic treatment of different regions of skin or of different organs such as different limbs, torso, and the like.

Figure 12:
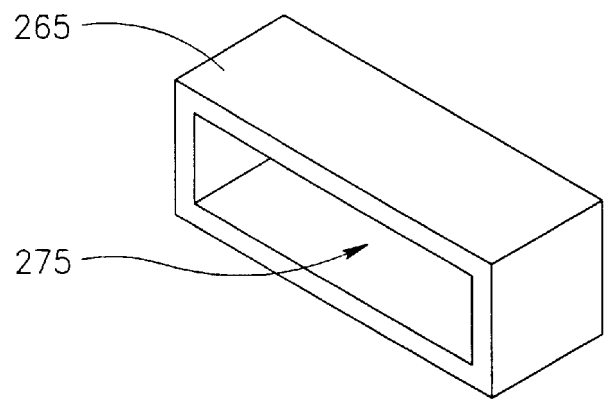
FIGS. 12–14 are schematic isometric views of three differently shaped extenders useful for hair removal when used with the apparatus of FIG. 12.
Figure 13:
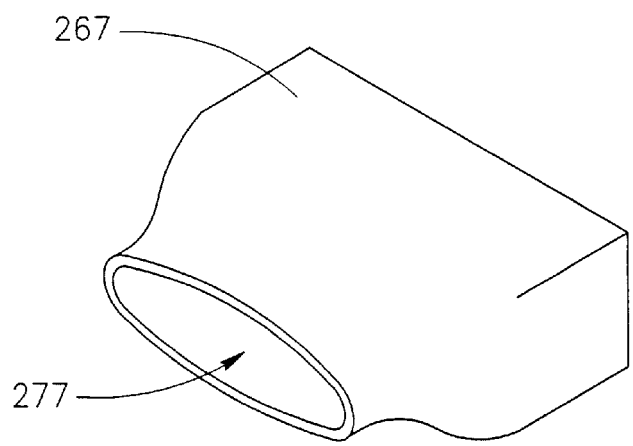
Figure 14:
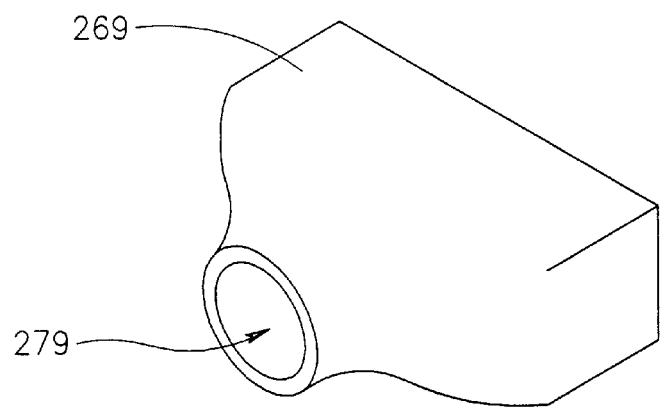

Reference is now made to FIGS. 12–14 which are schematic isometric views of three differently shaped extenders 265, 267 and 269 useful for performing photothermolysis when used with the apparatus 200 of FIG. 11. FIG. 12 illustrates an extender 265 having a rectangular aperture 275. FIG. 13 illustrates an extender 267 having an ellipsoidal aperture 277. FIG. 14 illustrates an extender 269 having a circular aperture 279. Each of the extenders 265, 267 and 269 may be used with the apparatus 200 for photothermolytic treatment of various skin regions.

It is noted that, the extenders 263, 265, 267 and 269 of FIGS. 11–14, respectively, may also include a sealing gasket (not shown) attached to the end of the extender distal from the apparatus 200 and made from a soft resilient material such as soft rubber, or any other suitable sealing material, for better sealing of the contact region with the skin (not shown). The extenders 263, 265, 267 and 269 of FIGS. 11–14, respectively, may or may not be internally coated with a diffusely reflective coating (not shown) for improving transmission of light through the apertures 219, 275, 277 and 279, within each of the corresponding extenders.

In accordance with a preferred embodiment of the present invention, the flash lamps 62, 63 and 64 may be disposable to allow convenient replacement of the lamp once it is burnt out.

It is noted that, while the preferred embodiments of the apparatuses 50, 100, 150 and 200 of FIGS. 7, 9, 10, and 11, respectively, have a housing shaped generally as a substantially rectangular open box, other embodiments are possible in which the housings have other shapes such as a cylindrical shape, a triangular prism shaped open box, a truncated triangular prism shaped open box or any other suitable shape having an open side and capable of forming a sealed cavity when suitably placed on the skin.

Figure 15:
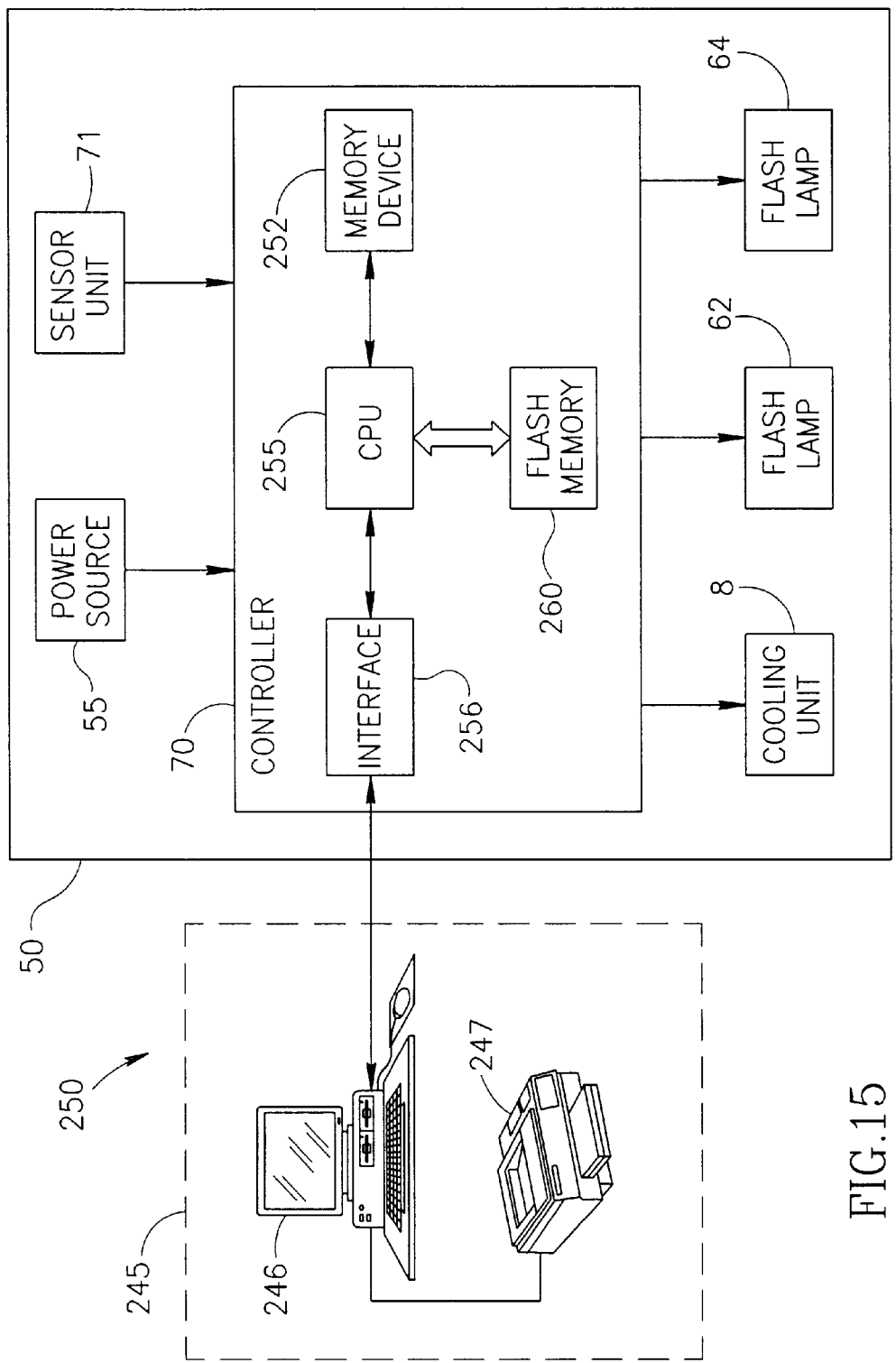
FIG. 15 is a schematic functional block diagram illustrating a programmable system including the apparatus for selective photothermolysis of FIG. 7, in accordance with still another preferred embodiment of the present invention.

Reference is now made to FIG. 15 which is a schematic functional block diagram illustrating a programmable system including the apparatus 50 for selective photothermolysis of FIG. 7, in accordance with still another preferred embodiment of the present invention. The system 250 includes the apparatus 50 of FIG. 7 and a programming device 245. The programming device 245 includes a computer 246 connected to a printer 247. The controller 70 includes a central processing unit (CPU) 265 connected to a memory device 252, an interface 256 and a removable memory device 260. The interface 256 can be a standard RS-232 interface or any other suitable serial or parallel interface device. The controller 70 is suitably connected to the power supply 55 and to the sensor unit 71 for sensing the temperature of the surface of the skin as disclosed in detail hereinabove. The memory device 252 is a read only memory integrated circuit, but can also be any other suitable type of electrical, magnetic, optical and magneto-optic storage or memory device, The controller 70 is also suitably connected to the cooling unit 8 and to the flash lamps 62 and 64 and controls their activation. It is noted that the controller 70 includes all the additional circuitry (not shown) necessary for interfacing with the sensing unit 71 and for controlling and energizing the cooling unit 8 and the flash lamps 62 and 64.

The program for operation of the controller 70 is stored, preferably, in the memory device 252. The treatment parameters, such as the skin temperature value at which the second pulse 82 (FIG. 8) is started, and the predetermined value of skin temperature at which the activation of the cooling device 8 is initiated, the pulse duration of the pulses 80 and 82 (FIG. 8), or (where relevant to the specific embodiment of the apparatus which is used) the time for switching on the pump, or any other parameters necessary for the operation of the controller 70, are, preferably, stored in flash memory 260.

In accordance with one preferred embodiment of the present invention, the controller 70 can be programmed by a physician in his office based on a test treatment made by the physician on the patient. Based on the results of the test treatment, the physician programs the treatment parameters to the necessary values by connecting the computer 246 to the controller 70 through the interface 256 and downloading the treatment parameters into the memory 252 or into the flash memory 260. The physician may additionally store the programmed treatment parameters, for future reference, on a storage device (not shown) included in the computer 246 such as a hard disk drive or any other suitable storage device. The physician may also generate a hard copy of the programmed treatment parameters, for example by printing a report on the printer 247.

Alternatively, the flash memory 260 can be physically removed from the controller 70 and the physician may program the treatment parameters by using a suitable programming interface (not shown) connected to a communication port (not shown) of the computer 246.

In accordance with another preferred embodiment of the present invention, the system 250 may be also used for remote programming of the treatment parameters by a physician. In this embodiment the user uses a video camera (not shown) or a digital camera (not shown) to remotely send a digital photograph of the treated area to his physician over the Internet using video-conferencing in real time or by sending a digital photograph as a data file using the internet or any other suitable data communication method. The physician receives the data or the digital photograph showing the results of the treatment and by examining the treatment results he may decide to change the treatment parameters. The physician then sends the new treatment parameters to the user over the internet, or by any other suitable data communication method as a data file. The user may then load the new parameters from the data file into the controller 70 erasing the previously stored parameters from and storing the new parameters on the flash memory 260. The advantage of this preferred embodiment of the invention is that the patient may obtain a treatment at home under the supervision of a doctor without having to physically visit the physicians office.

It is noted that while the embodiments disclosed hereinabove teaches the use of flash memory 256 as a preferred programmable and/or removable memory in the controllers 70 and 110 other types of memory devices such as eraseable programmable read only memory (EPROM), electrically eraseable programmable read only memory (EEPROM), magnetic bubble memory, or any reprogrammable and/or removable type of magnetic, optical, or magneto-optical memory devices may also be used instead of the flash memory 256.

It is noted that while the pump 66 of the apparatuses 50, 100, and 200 hereinabove, preferably operates by pumping air into the cavity overlying the skin for cooling the skin 60, the pump may also be adapted to pump another coolant. The coolant may be other gases such as $CO_2$ or a liquid coolant such as ethyl-chloride or any other suitable liquid coolant supplied from a suitable coolant container (not shown).

It is further noted that, the pump 66 of any of the apparatuses 50, 100, and 200 may be replaced by a reservoir (not shown) containing a coolant and having a valve (not shown) which is controlled by one of the controllers 70 or 110. The coolant may be a compressed gas or a liquid coolant. When one of the controllers 70 or 110 provides a suitable signal to the valve, the valve opens, and some the coolant exits the reservoir, expands, and enters the air cavity (not shown) of the apparatus 50, 100, or 200, respectively. The expansion of the compressed coolant lowers the coolant's temperature below ambient temperature and the coolant cools the skin 60 (not shown). The coolant in the reservoir may be a compressed $CO_2$ gas or any other suitable compressed gas, Alternatively, the coolant in the reservoir may be a liquid coolant such as ethyl-chloride or any other suitable liquid coolant.

It is noted that, the apparatuses 50, 100, 150 and 200, being hand held, portable devices directed for use by the user himself, have a size which allows them to fit into the palm of a hand. However, other preferred embodiments of the apparatus of the present invention are possible which are larger and do not fit in the palm of the hand.

It will be appreciated by the person skilled in the art that the invention is not limited to what has been disclosed hereinabove and illustrated in the drawings. While the invention has been described with respect to a limited number of embodiments, it will be appreciated that many variations, modifications and other applications of the invention may be made. For example, while the invention is particularly adapted for use in the treatment of psoriasis it may also be used with some modification to the treatment of varicose veins, port wine stains or any other treatment of humans or other animals which is amenable for treatment by selective photothermolysis methods.

What is claimed is:

1. Apparatus for selective photothermolysis of a target tissue within the skin, the apparatus comprising:
   a housing having an opening therein, said housing forming a cavity enclosing a volume of air when said opening is placed in contact with said skin;
   a pulsable heat source disposed within said housing for rapidly heating said volume of air to form a temperature gradient therealong;
   a pulsable source of narrow band electromagnetic radiation disposed within said housing for irradiating said skin with narrow band electromagnetic radiation to selectively heat said target tissue;
   a sensing unit attached to said housing for sensing the temperature of said skin tissue; and
   a controller that controls the heat source and the source of narrow band radiation to heat the skin to a first predetermined temperature, as sensed by the sensing unit, that is above 55° C. and then activates the pulsable source of narrow band radiation responsive to the sensing of said temperature.

2. The apparatus according to claim 1 wherein said cavity is a sealed cavity.

3. The apparatus according to claim 1 further including a pump suitably attached to said housing for controllably pumping air into said housing to displace said volume of air heated by said heat source with air having a temperature lower than the temperature of said volume of air, to prevent overheating of said skin.

4. The apparatus according to claim 3 wherein said pump is activated when said skin has reached a predetermined temperature after said heat source is energized.

5. The apparatus according to claim 1 wherein said heat source also provides pulsed light for irradiating said region of skin.

6. The apparatus according to claim 3 wherein said pulsed light is broad band pulsed light.

7. The apparatus according to claim 5 wherein said housing further includes a reflector for reflecting said pulsed broad band light and said narrow band electromagnetic radiation.

8. The apparatus according to claim 5 wherein at least part of said housing is coated by a layer of material having a high reflectivity for reflecting said pulsed broad band light and said narrow band electromagnetic radiation.

9. The apparatus according to claim 1 wherein said heat source is a flash lamp or an arc discharge lamp.

10. The apparatus according to claim 9 wherein the heat source is a flash lamp.

11. The apparatus according to claim 1 wherein said source of narrow band electromagnetic radiation includes a flash lamp or an arc discharge lamp and a filter attached to said housing and disposed between said flash lamp and said opening for absorbing a pre-selected portion of said pulsed broad band light, to produce narrow band electromagnetic radiation selectively absorbed by said target tissue.

12. The apparatus according to claim 11 wherein said target tissue is blood vessels within the skin and wherein said source of narrow band electromagnetic radiation emits radiation between the wavelengths of 550 to 610 nanometers.

13. Apparatus according to claim 1 wherein said first predetermined temperature is between about 55° C. and 65° C.

14. Apparatus according to claim 13 wherein the first predetermined temperature is above 60° C.

15. The apparatus according to claim 1 wherein said housing further comprises a sealing gasket attached to said housing along the circumference of said opening for forming a sealed air cavity disposed between said skin and said heat source.

16. Apparatus according to claim 1 wherein said controller terminates operation of said pulsable source of electromagnetic radiation when the sensed temperature of the target area reaches a second predetermined temperature that is greater than 70°.

17. Apparatus according to claim 16 wherein the second predetermined temperature is between about 70° C. and 75° C.

18. Apparatus according to claim 16 wherein the second predetermined temperature is above 75° C.

19. Apparatus according to claim 17 wherein the second predetermined temperature is below about 80° C.

20. Apparatus according to claim 17 wherein the second predetermined temperature is below about 90° C.

21. The apparatus according to claim 1 further including a cooling unit for controllably cooling said skin, to prevent overheating of said skin.

22. The apparatus according to claim 21 wherein said cooling unit is activated when said skin has reached a predetermined temperature after said heat source is energized.

23. The apparatus according to claim 21 wherein the controller is a programmable controller unit capable of receiving data determining at least one treatment parameter selected from a plurality of treatment parameters for coordinating the timing and the duration of activation of one or more of said heat source, said source of narrow band electromagnetic radiation and said cooling unit.

24. The apparatus according to claim 1 further including an extension, said extension having a first end attachable to said opening and a second end placeable on said skin, said extension has an aperture therethrough defining an area for treating said skin.

25. Apparatus according to claim 1 wherein the controller activates the heat source for a total time of less than 3 milliseconds.

26. The apparatus according to claim 1 wherein said housing is made of a heat insulating material.

27. Apparatus according to claim 1 wherein the controller activates the source of narrow band radiation for a period of between 0.5 and 5 milliseconds.

28. Apparatus according to claim 27 wherein the energy delivered to the skin by the source of narrow band radiation is between about 0.5 and 3 J/cm$^2$.

29. The apparatus according to claim 1 and including an electrical power source for activating said heat source and said source of narrow band radiation.

30. The apparatus according to claim 29 wherein said at least one power source comprises at least one battery, at least one capacitor and an electronic control circuit.

31. The apparatus according to claim 29 wherein said at least one power source comprises a mains operated direct current supply, at least one capacitor and an electronic control circuit.

32. The apparatus according to claim 1 wherein said sensor unit includes at least one optical sensor wherein said at least one optical sensor receives infra-red radiation emanating from an area of said skin positioned under said housing, senses the intensity of said infra-red radiation and provides signals indicative of said intensity to said controller.

33. The apparatus according to claim 32 wherein said at least one optical sensor includes an infra-red light sensitive photo-diode.

34. The apparatus according to claim 1 wherein said sensor unit includes at least one contact temperature sensor for contacting said skin to sense the temperature of said skin.

35. The apparatus according to claim 34 wherein said at least one contact temperature sensor is a thermistor.

36. The apparatus according to claim 1 which fits into the palm of a hand.

37. The apparatus according to claim 1 wherein the controller is a programmable controller unit capable of receiving data determining at least one treatment parameter selected from a plurality of treatment parameters for coordinating the timing and the duration of activation of one or both of said heat source and said source of narrow band electromagnetic radiation.

38. The apparatus according to claim 37 wherein said programmable controller unit includes a removable storage device on which said plurality of treatment parameters are stored, said removable storage device is capable of being disconnected and removed from said programmable controller for changing the value of at least one of said plurality of treatment parameters, prior to reconnecting said storage device to said programmable controller.

39. The apparatus according to claim 38 wherein said storage device is selected from a flash memory device, a magnetic bubble memory device, an EPROM memory device, an EEPROM memory device, an optical memory device, an opto-magnetic memory device and a magnetic memory device.

40. A method for selective photothermolysis of a target tissue within the skin, the method comprising the steps of:
   providing a cavity formed by a housing overlying said skin, said cavity comprising a volume of air having a first end proximal to said skin and a second end distal to said skin;
   heating said skin by pulsing a heat source disposed within said cavity to heat the air surrounding said heat source to create a temperature gradient in said volume of air, said temperature gradient having a first temperature at said first end and a second temperature at said second end, said first temperature being lower than said second temperature;
   continuously monitoring the surface temperature of said skin;
   irradiating said skin with a pulse of narrow band electromagnetic radiation when the surface temperature of said skin reaches a first predetermined value, said pulse having a duration sufficient to selectively raise the temperature of said target tissue to the coagulation temperature of said target tissue without coagulating the skin tissue surrounding said target tissue; and
   terminating said step of heating of said skin.

41. The method according to claim 40 wherein said step of terminating comprises manually lifting said housing away from said skin to allow air at room temperature to cool said skin.

42. The method according to claim 40 wherein said step of terminating comprises the step of activating a cooling unit to cool said skin to prevent overheating of said skin.

43. The method according to claim 42 wherein said step of terminating comprises activating said cooling unit when the surface temperature of said skin reaches a second predetermined value.

44. The method according to claim 40 wherein said air cavity is a sealed air cavity disposed between said housing and said skin.

45. The method according to claim 40 wherein said heat source is a flash lamp or a gas discharge lamp and wherein said step of heating further includes the step of additionally heating said skin by irradiating said skin with broad band incoherent radiation produced by said flash lamp or gas discharge lamp.

46. The method according to claim 45 wherein said step of additionally heating further includes the step of filtering said broad band incoherent radiation, prior to irradiating said skin therewith, to remove a preselected portion thereof, said pre-selected portion includes radiation in the ultra-violet light range which may be harmful to said skin.

47. The method according to claim 40 wherein said target tissue is blood vessels within psoriatic skin and wherein said pulse of narrow band electromagnetic radiation comprises radiation between the wavelengths of 550 to 610 nanometers.

48. The method according to claim 40 wherein said first predetermined value is between 55° C. and 65° C., and wherein said coagulation temperature is between 70° C. and 90° C.

49. The method according to claim 40 wherein said step of terminating comprises automatically pumping a coolant into said cavity of said housing when the surface temperature of said skin reaches a second predetermined value.

50. The method according to claim 40 wherein said step of terminating comprises automatically pumping air at a temperature lower than the temperature of the surface of said skin into said cavity of said housing when the surface temperature of said skin reaches a second predetermined value.

51. Apparatus for selective photothermolysis of a skin target tissue, the apparatus comprising:
   a pulsable heat source operative to heat the skin target tissue and skin surrounding the target tissue to a temperature below a coagulation temperature; and
   a pulsable source of narrow band electromagnetic radiation which irradiates the target tissue and said surrounding tissue with narrow band electromagnetic radiation to selectively heat said target tissue to a temperature above said coagulation temperature, as compared to said surrounding tissue, which remains below the coagulation temperature.

52. Apparatus according to claim 51 wherein the pulsable heat source forms a temperature gradient in the air between the source and the skin, said heat source being at a temperature high enough to burn the skin.

53. Apparatus according to claim 52 and including a housing having an opening therein, said housing forming a cavity enclosing a volume of air when said opening is placed in contact with said skin.

54. Apparatus according to claim 53 and including:
   a sensor unit for sensing the temperature of said skin temperature.

55. Apparatus according to claim 54 and including:
   a controller unit which controls said heat source and said source of electromagnetic radiation, for coordinating the sequence of activation of said heat source and said source of electromagnetic radiation responsive to said sensed temperature.

56. Apparatus according to claim 55 further including a pump attached to said housing and controlled by said controller for controllably pumping a cooler gas into said housing to displace said volume of air heated by said heat source with air having a temperature lower than the temperature of said volume of air, to prevent said surrounding tissue from rising above said coagulation temperature.

57. Apparatus according to claim 56 wherein said pump is activated by said controller when said skin has reached a predetermined temperature after said heat source is energized.

58. Apparatus according to claim 53 and including a cooling unit suitably attached to said housing and controlled by said controller for controllably cooling said skin, to prevent overheating of said skin.

59. Apparatus according to claim 58 wherein said cooling unit is activated by said controller when said skin has reached a predetermined temperature after said heat source is energized.

60. Apparatus according to claim 51 wherein said heat source comprises a source of broadband electromagnetic radiation which heats the skin.

61. Apparatus according to claim 51 and including:
   a sensor unit for sensing the temperature of said skin.

62. Apparatus according to claim 61 wherein said sensor unit includes at least one optical sensor, said at least one optical sensor receiving infra-red radiation emanating from an area of said skin positioned under said housing, sensing the intensity of said infra-red radiation and providing a signal indicative of said intensity.

63. Apparatus according to claim 62 wherein said at least one optical sensor includes an infra-red light sensitive photo-diode.

64. Apparatus according to claim 61 wherein said sensor unit comprises at least one contact temperature sensor for contacting said skin, and for providing signals indicative of said temperature.

65. Apparatus according to claim 61 and including:
   a controller unit which controls said heat source and said source of electromagnetic radiation, for coordinating the sequence of activation of said heat source and said source of electromagnetic radiation responsive to said sensed temperature.

66. Apparatus according to 65 wherein said controller unit has a data input capable of receiving data determining at least one treatment parameter selected from a plurality of treatment parameters for coordinating the timing and the duration of activation of any of said heat source and said source of narrow band electromagnetic radiation.

67. Apparatus for selective photothermolysis of a target tissue within the skin, the apparatus comprising:
   a housing having an opening therein, said housing forming a cavity enclosing a volume of air when said opening is placed in contact with said skin;
   a pulsable heat source disposed within said housing for rapidly heating said volume of air to form a temperature gradient therealong;
   a pulsable source of narrow band electromagetic radiation disposed within said housing for irradiating said skin with narrow band electromagnetic radiation to selectively heat said target tissue;
   cooling means for cooling said skin; and
   a controller that activates the source of narrow band electromagnetic radiation when the temperature of the skin rises above a predetermined value.

68. The apparatus according to claim 67 and including a sensing unit for sensing the temperature of said skin.

69. The apparatus according to claim 67 wherein the means for cooling comprises a pump suitably attached to said housing for controllably pumping air into said housing to displace said volume of air heated by said heat source with air having a temperature lower than the temperature of said volume of air, to prevent overheating of said skin.

70. Apparatus for selective photothermolysis of a target tissue, the apparatus comprising:
- a housing having an opening therein, said housing forming a cavity enclosing a volume of air when said opening is placed in contact with said skin;
- a pulsable heat source disposed within said housing for rapidly heating said volume of air to form a temperature gradient therealong;
- a pulsable source of narrow band electromagnetic radiation disposed within said housing for irradiating said skin with narrow band electromagnetic radiation to selectively heat said target tissue; and
- a controller that activates the heat source for a total period of between 1 and 3 milliseconds prior to activating the pulsable source of narrow band electromagnetic radiation.

71. Apparatus for selective photothermolysis of a target tissue within the skin, the apparatus comprising:
- a housing having an opening therein, said housing forming a cavity enclosing a volume of air when said opening is placed in contact with said skin;
- a flash lamp heat source disposed within said housing for rapidly heating said volume of air to form a temperature gradient therealong; and
- a pulsable source of narrow band electromagnetic radiation disposed within said housing for irradiating said skin with narrow band electromagnetic radiation to selectively heat said target tissue.

72. Apparatus according to claim 71 comprising:
- a sensor that senses the temperature of the skin;
- a controller that controls activation of the flash lamp and the pulsable source of narrow band radiation and receives indications of the skin temperature from the sensor,
- wherein the controls monitors the temperature, after cessation of the operation of the flash lamp and activates the pulsable source of narrow band radiation when the skin temperature reaches a first predetermined temperature.

73. Apparatus according to claim 72 wherein the controller ceases activation of the pulsable source of narrow band radiation when the target tissue reaches a second predetermined temperature.

74. Apparatus according to claim 72 and including means for cooling the skin, wherein the controller activates the cooling means to prevent heating of the skin above a temperature which would cause damage to the surrounding tissue.

75. The apparatus according to claim 74 wherein said flash lamp is a glass xenon lamp.

76. The apparatus according to claim 74 wherein said flash lamp is disposable.

77. The apparatus according to claim 74 wherein said flash lamp is a quartz xenon lamp and wherein said apparatus further includes a filter attached to said housing and disposed between said flash lamp and said opening for absorbing a pre-selected portion of said pulsed broad band light, said pre-selected portion includes radiation in the ultra-violet light range which may be harmful to said skin.

78. Apparatus for selective photothermolysis of a target tissue within the skin, the apparatus comprising:
- a housing having an opening therein, said housing forming a cavity enclosing a volume of air when said opening is placed in contact with said skin;
- a pulsable heat source disposed within said housing for rapidly heating said volume of air to form a temperature gradient therealong;
- a pulsable source of narrow band electromagnetic radiation disposed within said housing for irradiating said skin with narrow band electromagnetic radiation to selectively heat said target tissue;
- a sensing unit attached to said housing for sensing the temperature of said skin; and
- a programmable controller unit capable of controlling the activation of said heat source and said source of electromagnetic radiation and of receiving data determining at least one treatment parameter selected from a plurality of treatment parameters for coordinating the timing and the duration of activation of any of said heat source and said source of narrow band electromagnetic radiation.

79. Apparatus for selective photothermolysis of a target tissue within the skin, the apparatus comprising:
- a housing having an opening therein, said housing forming a cavity enclosing a volume of air when said opening is placed in contact with said skin;
- a pulsable heat source disposed within said housing for rapidly heating said volume of air to form a temperature gradient therealong, the temperature of the air adjacent the heat source having a temperature high enough to burn the tissue; and
- a pulsable source of narrow band electromagnetic radiation disposed within said housing for irradiating said skin with narrow band electromagnetic radiation to selectively heat said target tissue.

80. Apparatus according to claim 79 and including a sensing unit for sensing the temperature of said skin.

81. Apparatus according to claim 80 wherein the pulseable narrow band source is activated responsive to a measurement of skin temperature above a predetermined value.

82. Apparatus according to claim 80 and including means for cooling the skin, said means for cooling being activated in response to a measurement of skin temperature above a predetermined value.

83. Apparatus according to claim 82 wherein the means for cooling comprises a pump for controllably bringing a cooler gas into said housing to displace said volume of air heated by said heat source with air having a temperature lower than the temperature of said volume of air.

84. A method of photothermolysis, comprising:
- heating a target area of the skin and a surrounding area by conduction of heat through air contacting the skin to a temperature above 55° C.; and
- then selectively heating the target area to a coagulation temperature while the surrounding area remains below the coagulation temperature.

85. A method according to claim 84 wherein selectively heating comprises irradiating at least the target area with narrow band electromagnetic radiation.

86. A method according to claim 85 wherein the surrounding area is also irradiated by the narrow band electromagnetic radiation, which radiation is selectively absorbed by the target tissue.

87. A method according to claim 85 wherein heating the target area comprises conducting heat from a heat source spaced from the skin.

88. A method according to claim 87 wherein the heat source is a flash lamp.

89. Apparatus according to claim 1 wherein said heat source and said source of narrow band radiation are activated substantially simultaneously.

* * * * *